(12) United States Patent
Anderson et al.

(10) Patent No.: US 10,525,333 B2
(45) Date of Patent: Jan. 7, 2020

(54) TECHNIQUES FOR LOW POWER MONITORING OF SPORTS GAME PLAY

(71) Applicant: INTEL CORPORATION, Santa Clara, CA (US)

(72) Inventors: Glen J. Anderson, Beaverton, OR (US); Jose K. Sia, Jr., Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 16/005,047

(22) Filed: Jun. 11, 2018

(65) Prior Publication Data

US 2019/0009170 A1 Jan. 10, 2019

Related U.S. Application Data

(63) Continuation of application No. 14/497,024, filed on Sep. 25, 2014, now Pat. No. 9,993,723.

(51) Int. Cl.
*A63F 13/216* (2014.01)
*A63F 13/21* (2014.01)
(Continued)

(52) U.S. Cl.
CPC ............ *A63F 13/21* (2014.09); *A61B 5/1113* (2013.01); *A61B 5/6801* (2013.01);
(Continued)

(58) Field of Classification Search
CPC ................. A63F 13/235; A63F 13/327; A63F 2300/405; A63F 2300/406
See application file for complete search history.

(56) References Cited

U.S. PATENT DOCUMENTS 5,214,789 A * 5/1993 George ................. H04W 4/029
455/440
6,052,598 A * 4/2000 Rudrapatna ........... H04W 4/029
455/456.1
(Continued)

FOREIGN PATENT DOCUMENTS

CN 1672755 A 9/2005
CN 101099893 A 1/2006
(Continued)

*Primary Examiner* — Steven J Hylinski

(57) ABSTRACT

Various embodiments are directed to techniques for reducing electric power employed by devices of a game play monitoring system that collects data during game play in a sport. An apparatus may include an interaction detection component to monitor an interaction sensor of a playing piece to detect an interaction with a body, generate playing piece data recording an aspect of the interaction and determine whether the interaction maintains the playing piece within a close proximity to the body; and a communications component to use electric power from a power source to wirelessly transmit the playing piece data to a player device carried by the body via shorter range wireless communications or to an access point device via longer range wireless communications based on the determination, the shorter range wireless communications to consume electric power of the power source at a lesser rate. Other embodiments are described and claimed.

23 Claims, 11 Drawing Sheets

(51) Int. Cl.

| | | |
|---|---|---|
| *A63B 24/00* | (2006.01) | |
| *A63F 9/24* | (2006.01) | |
| *A61B 5/00* | (2006.01) | |
| *A61B 5/11* | (2006.01) | |
| *H04W 52/02* | (2009.01) | |
| *H04W 4/029* | (2018.01) | |
| *H04W 4/80* | (2018.01) | |

(52) U.S. Cl.
CPC ............ *A61B 5/6887* (2013.01); *A63B 24/00* (2013.01); *A63F 9/24* (2013.01); *H04W 4/029* (2018.02); *H04W 4/80* (2018.02); *H04W 52/0254* (2013.01); *H04W 52/0261* (2013.01); *A61B 5/681* (2013.01); *A61B 5/6895* (2013.01); *A61B 2560/0209* (2013.01); *A61B 2562/0219* (2013.01); *A63B 2225/50* (2013.01); *A63B 2225/54* (2013.01); *Y02D 70/00* (2018.01); *Y02D 70/1224* (2018.01); *Y02D 70/1244* (2018.01); *Y02D 70/1246* (2018.01); *Y02D 70/1262* (2018.01); *Y02D 70/142* (2018.01); *Y02D 70/144* (2018.01); *Y02D 70/146* (2018.01); *Y02D 70/162* (2018.01); *Y02D 70/166* (2018.01); *Y02D 70/26* (2018.01)

(56) References Cited

U.S. PATENT DOCUMENTS

| | | | | |
|---|---|---|---|---|
| 6,826,607 | B1* | 11/2004 | Gelvin | B60R 25/1004 709/224 |
| 7,085,576 | B2 | 8/2006 | Ranganathan | H04L 65/4092 455/456.1 |
| 7,130,743 | B2* | 10/2006 | Kudo | G01C 21/3617 701/424 |
| 7,359,713 | B1* | 4/2008 | Tiwari | G01S 19/34 455/456.1 |
| 7,653,400 | B2 | 1/2010 | Robertson | H04W 64/006 342/457 |
| 7,840,227 | B2* | 11/2010 | Kahlert | H04W 36/32 370/331 |
| 7,848,270 | B2* | 12/2010 | Hilmersson | G08C 17/00 370/311 |
| 8,914,036 | B2* | 12/2014 | Kitani | H04W 48/18 455/456.1 |
| 9,161,172 | B2* | 10/2015 | Poduri | H04W 4/029 |
| 9,301,277 | B2* | 3/2016 | Fujimoto | H04W 64/006 |
| 9,699,618 | B2* | 7/2017 | Singh | H04W 4/029 |
| 10,341,693 | B2* | 7/2019 | Barr | H04W 36/32 |
| 2002/0077189 | A1 | 6/2002 | Tuer et al. | |
| 2003/0065712 | A1* | 4/2003 | Cheung | H04L 29/06 709/203 |
| 2003/0119504 | A1* | 6/2003 | Rankin | H04W 36/24 455/434 |
| 2003/0122708 | A1* | 7/2003 | Percy | G01S 5/0027 342/357.52 |
| 2005/0221829 | A1* | 10/2005 | Nishida | G01S 11/06 455/440 |
| 2006/0143645 | A1* | 6/2006 | Vock | A43B 3/00 725/9 |
| 2006/0286988 | A1* | 12/2006 | Blume | G01C 21/3679 455/456.1 |
| 2007/0115883 | A1* | 5/2007 | Narayanan | H04W 36/0011 370/331 |
| 2007/0133469 | A1* | 6/2007 | Shin | H04W 40/34 370/331 |
| 2008/0143484 | A1* | 6/2008 | Twitchell | G06Q 10/08 340/10.1 |
| 2008/0318625 | A1* | 12/2008 | Rofougaran | A63F 13/235 455/556.1 |
| 2009/0002316 | A1* | 1/2009 | Rofougaran | A63F 13/12 345/156 |
| 2009/0227266 | A1* | 9/2009 | Baik | G01S 5/0294 455/456.1 |
| 2009/0284368 | A1* | 11/2009 | Case, Jr. | A43B 3/0005 340/539.1 |
| 2010/0137053 | A1* | 6/2010 | Blair | G06Q 20/3224 463/17 |
| 2010/0279708 | A1* | 11/2010 | Lidsrom | H04W 4/029 455/456.1 |
| 2010/0279776 | A1* | 11/2010 | Hall | H04W 4/029 463/42 |
| 2011/0164546 | A1* | 7/2011 | Mishra | H04W 40/026 370/312 |
| 2012/0108326 | A1* | 5/2012 | Hall | A63F 13/79 463/29 |
| 2012/0128172 | A1* | 5/2012 | Alden | H04L 63/0492 381/77 |
| 2012/0155426 | A1* | 6/2012 | Verma | H04W 36/0033 370/331 |
| 2012/0302162 | A1* | 11/2012 | Chueh | H04L 67/1095 455/39 |
| 2013/0310055 | A1 | 11/2013 | Dewing | |
| 2014/0106677 | A1* | 4/2014 | Altman | H04W 4/80 455/41.2 |
| 2014/0143038 | A1* | 5/2014 | Tropper | A61B 5/1118 705/14.19 |
| 2014/0278044 | A1* | 9/2014 | Jacobs | G06F 17/00 701/300 |
| 2015/0120930 | A1* | 4/2015 | Kamthe | H04W 48/20 709/226 |
| 2015/0304929 | A1* | 10/2015 | Hua | H04W 36/32 455/436 |
| 2016/0021508 | A1* | 1/2016 | Dunkin | H04L 67/2847 701/518 |

FOREIGN PATENT DOCUMENTS

| | | | | |
|---|---|---|---|---|
| CN | 2815442 Y | 9/2006 | | |
| CN | 101454812 A | 6/2009 | | |
| CN | 101689041 A | 3/2010 | | |
| CN | 101835513 A | 9/2010 | | |
| JP | 2012510873 A | 5/2012 | | |
| WO | WO-2008083757 A1 * | 7/2008 | ......... | G01C 21/3655 |
| WO | WO-2014081956 A2 * | 5/2014 | ........... | G06F 1/3206 |

* cited by examiner

TECHNIQUES FOR LOW POWER MONITORING OF SPORTS GAME PLAY

CROSS-REFERENCE TO RELATED APPLICATIONS

This application is a continuation of, claims the benefit of and priority to previously filed U.S. patent application Ser. No. 14/497,024 filed Sep. 25, 2014, entitled "TECHNIQUES FOR LOW POWER MONITORING OF SPORTS GAME PLAY", the subject matter of which is incorporated herein by reference in its entirety.

BACKGROUND

It has become commonplace for players and playing pieces in sports to be equipped with wireless devices to acquire data concerning game play, especially in team sports such as basketball, soccer, football, hockey, etc. Although such game play may be tracked with cameras, there can be moments when multiple players are in such close proximity to a playing piece (e.g., a ball or a puck) that it becomes at least difficult to discern which player has control over or is otherwise interacting with the playing piece at any given time. As familiar to many who participate in or at least closely follow various team sports, statistical information concerning which player(s) have interacted with the playing piece during the course of game play can be of significance in analyzing the performance of players and/or teams of players. Such performance analysis is often an input in coaching players and/or in selecting players to join a team.

Such wireless devices as are worn by players and/or integrated into playing pieces are often powered with batteries. This often places considerable limitations on the amount of power available to operate the sensors that gather data and to operate the transmitters that transmit the data. While such limitations could be reduced if larger batteries could be used with wireless devices carried on the bodies of players, the additional weight of larger batteries may encumber the very player performance to be monitored. Also, while such limitations could correspondingly be reduced if larger batteries could be used with a wireless device incorporated into a playing piece, the playing pieces used in many sports are tightly regulated in terms of their shape, size and weight such that the use of larger batteries may cause the playing piece to exceed one or more of these specifications.

DETAILED DESCRIPTION

Figure 1:
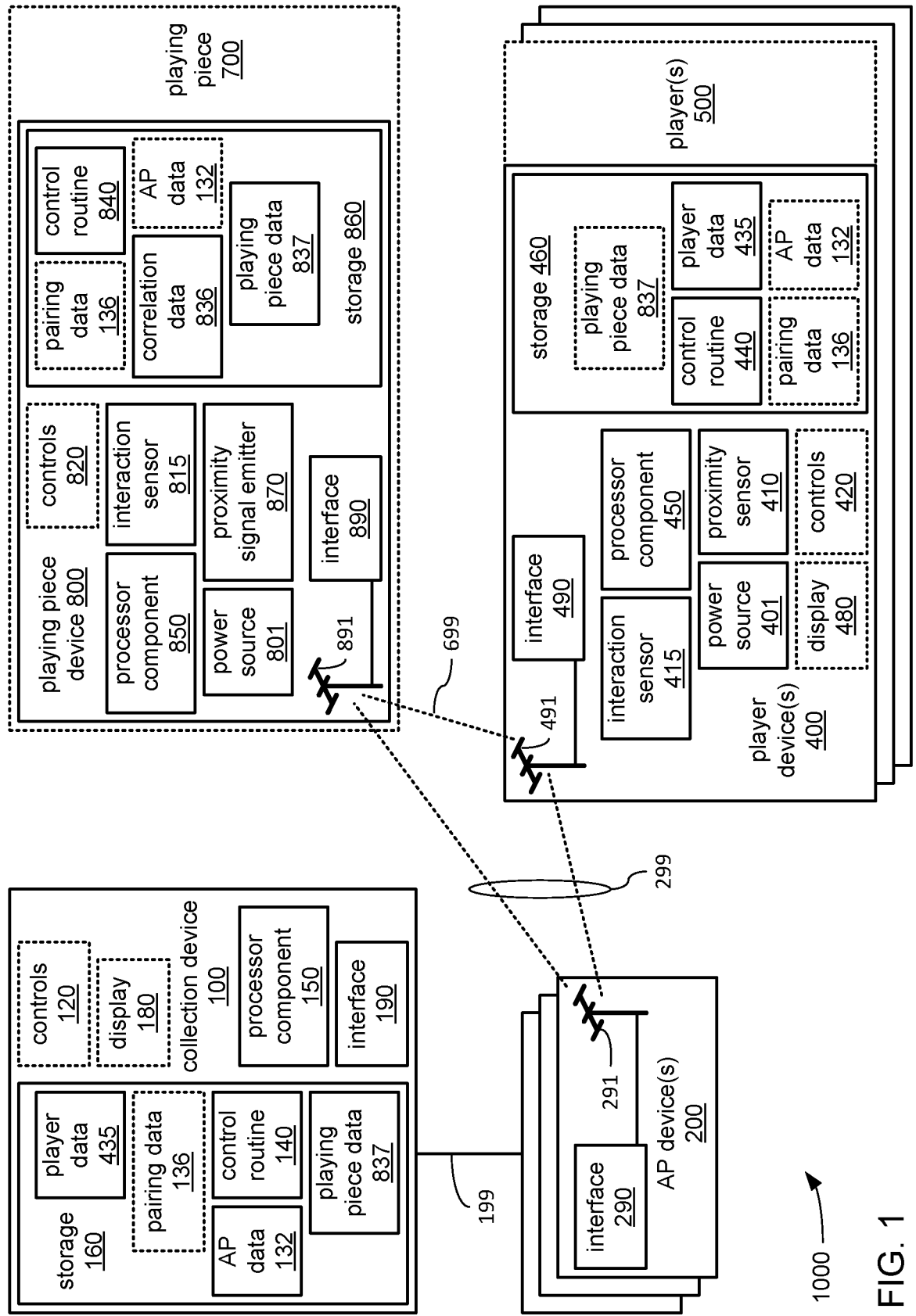
FIG. 1 illustrates an embodiment of a game play monitoring system.

Various embodiments are generally directed to techniques for reducing the amount of electric power employed in player devices and/or a playing piece device of a game play monitoring system that collects data during game play in a sport. In a game play monitoring system, the use of electric power to transmit collected data and/or the use of types of wireless communications that consume electric power at a higher rate may be conditioned on the proximity of a player to a playing piece, interaction between a player and a playing piece, location within a playing area and/or distances by which a playing piece is moved. More specifically, power may be removed from a transmitter of a player device at a time when a player is neither proximate to nor interacting with a playing piece. Alternatively or additionally, a type of wireless communications that consumes electric power at a lower rate may be employed by a playing piece device when the playing piece is proximate to a player such that data collected by the playing piece device is able to be relayed through a player device.

The player device(s) worn or otherwise carried by on portions of the body or bodies of one or more players may collect and wirelessly transmit data concerning aspects of game play to a collection device of the game play monitoring system through one or more access point (AP) devices positioned about a playing area. The playing piece device incorporated into or otherwise carried by a playing piece may also collect and wirelessly transmit data concerning aspects of game play to the collection device. However, at different times, the playing piece device may transmit data to the collection device either more directly through the one or more AP devices, or through a combination of a player device and one or more AP devices.

Each player device may be a wireless device worn by a player or incorporated into a portion of a uniform or other article of clothing or equipment that is worn or otherwise carried by a body portion of a player. Each player device may incorporate any of a variety of types of sensors to detect various aspects of a player's actions during game play, including aspects of the player's proximity to a playing piece, the player's interaction with the playing piece, and/or aspects of the player's own physical condition. In some embodiments, the player device may be of a single-piece construction in which all of its components are enclosed within a single casing. In other embodiments, the player device may be made up of two or more pieces distributed about different portions of a player's body. Such distributed positioning may serve to distribute sensors or components of sensors about different locations on the player's body. Such distributed portions of a player device may be linked with electrically and/or optically conductive cabling, and/or may be linked wirelessly.

Each player device may be capable of multiple types of wireless communication, including a longer range type of wireless communications that consumes electric power at a higher rate and a shorter range type of wireless communications that consumes electric power at a lower rate. The longer range type of communications may be selected to reach the location(s) of the one or more AP devices to enable the transmission of collected data directly thereto. The shorter range type of communications may be selected to reach the playing piece device at times when the playing piece is proximate to the body of a player carrying the player device on a portion of their body to enable reception of data collected by the playing piece device that is to be relayed to the one or more AP devices through use of the longer range type of communications.

Each player device may condition the provision of electric power for either or both of the longer range and lower power types of communications on detecting one or both of proximity to the playing piece and interaction with the playing piece. More specifically, each player device may conserve electric power by refraining from transmitting collected data until the playing piece is proximate to the body of a player carrying the player device and/or the body of that player is interacting with the playing piece. Conditioning the transmission of collected data in this manner may be based on an assumption that, unless a player is proximate to and/or interacting with a playing piece as part of game play, no data of interest may be collected by the sensors. Indeed, the operation of one or more of the sensors to collect data may also be similarly conditioned.

The playing piece device may be a wireless device attached to, incorporated into or otherwise carried by a playing piece used in game play, such as a ball or puck. In some embodiments, the playing piece may be manufactured or otherwise fabricated with the playing piece device incorporated within it. The playing piece device may incorporate any of a variety of types of sensors to detect various aspects of interaction with players and/or movement imparted to the playing piece by such interaction during game play.

Not unlike the player device(s), the playing piece device may be capable of multiple types of wireless communication, including a longer range type of wireless communications that consumes electric power at a higher rate and a shorter range type of wireless communications that consumes electric power at a lower rate. The shorter and longer range types of communications selected for use by the playing piece device may conform to similar specifications as the shorter and longer range types of communications selected for use by the player devices to enable interoperability among the player devices, the player piece device and the AP device(s). The shorter range type of communications may be selected to reach the player device(s) carried on body portions of one or more players at times when the playing piece is in relatively close proximity to the body of a player that carries a player device to enable transmission of data collected by the playing piece device thereto for relaying by that player device to the one or more AP devices through use of the longer range type of communications. However, at times when the playing piece is not in relatively close proximity to the body of a player that a player device such that there is no player device of the game play monitoring system that is within range of the shorter range type of communications, the longer range type of communications may be selected to reach the location(s) of the one or more AP devices to enable the transmission of collected data directly thereto.

The playing piece device may condition the use of the longer range type of communications over the shorter range type of communications on detecting a type of movement imparted to the playing piece by interaction therewith that likely precludes the playing piece remaining in close proximity to any one player such that the shorter range type of communications may be used to transmit collected data. More specifically, the playing piece device may conserve electric power by using the shorter range type of communications except upon detecting movement in which the playing piece is caused to travel a sufficiently lengthy distance and/or at a sufficiently high speed that it is deemed unlikely that the playing piece is able to remain in relatively close proximity to any one player to enable transmission of collected data to a player device carried on the body of that player via the shorter range type of communications. During such movement characterized by relatively lengthy travel, the longer range type of communications may be the only one of the two types that is able to reach any other device.

Conditioning the selection of type of communications in this manner may be based on an assumption that, while each player may interact with the playing piece on a relatively episodic basis, the playing piece may be interacted with quite frequently and/or for extended periods of time. Stated differently, the playing piece may be expected to frequently collect a considerable amount of data concerning interactions with the playing piece by multiple players such that the playing piece device may need to transmit collected data more frequently than any of the player devices. Use of a shorter range type of communications by the playing piece device, when possible, to transmit collected data to one or more of the player devices to relay to the collection device offloads the use of the longer range type of communications to the player devices that may otherwise not need to transmit collected data as frequently may reduce the overall rate of consumption of electric power by the playing piece device. In essence, the playing piece device opportunistically offloads the use of the longer range type of communications to the player devices.

One or more of the player devices may employ an analysis of signals received from multiple ones of the AP devices (e.g., signals exchanged as part of engaging in the longer range type of communications) to recurringly determine their locations within the playing area. The player devices may also analyze signals received from AP devices to determine a level of quality of the longer range type of communications available at different locations within the playing area, and may provide indications of those levels of quality to the playing piece device. Alternatively, the playing piece device may perform the analysis of signals from the AP devices to determine current locations and/or level of quality of the longer range type of communications possible at those locations. The playing piece device may, over time, correlate locations within a playing area with different levels of quality of the longer range type of communications available at those locations. More specifically, the playing piece device may eventually "learn" that one location within the playing area is not well covered by the AP devices such that the playing piece device may refrain from transmitting collected data via the longer range type of communications until it is within another location that is better covered by the AP devices.

More broadly, the playing piece integrating a playing piece device may be an object of a wide variety of types of interaction object that may be interacted with by a person or machine that carries a player device while in relatively close proximity thereto. Also more broadly, the player carrying a player device may be person or machine that may participate in any of a variety of interactions with the interaction device while in relatively close proximity thereto. Upon detecting interaction with such a participant that may tend to keep the interaction object within relatively close proximity thereto, the interaction object may employ a type of shorter range wireless communications that consumes electric power at a lower rate to communicate with the player device carried by that participant. However, upon detecting a form of interaction deemed likely to place the object into relatively lengthy travel such that it is deemed likely to no longer be in relatively close proximity to any such participant, the object may cease to employ the shorter range wireless communications in favor of employing a type of longer range wireless communications. Thus, although the discussion herein focuses largely on embodiments in which the object is a playing piece that is interacted with by one or more participants that are persons interacting with the interaction object in game play, the presentation of such embodiments herein should not be deemed to be so limiting.

With general reference to notations and nomenclature used herein, portions of the detailed description which follows may be presented in terms of program procedures executed on a computer or network of computers. These procedural descriptions and representations are used by those skilled in the art to most effectively convey the substance of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, these manipulations are often referred to in terms, such as adding or comparing, which are commonly associated with mental operations performed by a human operator. However, no such capability of a human operator is necessary, or desirable in most cases, in any of the operations described herein that form part of one or more embodiments. Rather, these operations are machine operations. Useful machines for performing operations of various embodiments include general purpose digital computers as selectively activated or configured by a computer program stored within that is written in accordance with the teachings herein, and/or include apparatus specially constructed for the required purpose. Various embodiments also relate to apparatus or systems for performing these operations. These apparatus may be specially constructed for the required purpose or may include a general purpose computer. The required structure for a variety of these machines will appear from the description given.

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives within the scope of the claims.

FIG. 1 illustrates a block diagram of a game play monitoring system 1000 incorporating one or more of a collection device 100, one or more access point (AP) devices 200, one or more player devices 400 and/or a playing piece device 800. As depicted, the playing piece device 800 may be incorporated into a playing piece 700 interacted with by the body or bodies 500 of one or more players in the play of a game within a playing area. More specifically, the playing piece 700 may be a ball or puck into which playing piece device 800 is installed or otherwise incorporated. As also depicted, portions of each player's body 500 may carry at least one player device 400. More specifically, each player's body 500 may wear or otherwise carry one or more player devices 400 on one or more portions of their bodies 500, or the player devices 400 may be incorporated into uniforms or other clothing items or playing equipment worn or otherwise carried somewhere on portions of the players' bodies 500.

The player device(s) 400 may collect player data 435 concerning the participation of respective ones of the player that carry one or more of the player devices 400 on one or more portions of their bodies 500. Each player device 400 may transmit its player data 435 to the collection device 100 via a longer range wireless network 299 formed with the one or more AP devices 200 operated by the collection device 100. The player data 435 may be relayed by one of the one or more AP devices 200 to the collection device 100 via a network 199. The playing piece device 800 may collect playing piece data 837 concerning interactions with the playing piece 700. On occasions in which the playing piece 700 and a player's body 500 are in relatively close proximity to each other as to be within range of shorter range communications, the playing piece device 800 may transmit the playing piece data 837 to a player device 400 carried on a body portion of that player via a shorter range wireless network 699 formed therebetween. That player device 400 may then relay the playing piece data 837 to the collection device 100 via the longer range wireless network 299, the one or more AP devices 200 and the network 199. On other occasions, the playing piece device 800 may more directly transmit the playing piece data 837 to the collection device 100 via the longer range wireless network 299, the one or more AP devices 200 and the network 199.

More generally, each of these devices 100, 200, 400 and 800 may be any of a variety of types of computing device, including without limitation, a desktop computer system, a data entry terminal, a laptop computer, a netbook computer, a tablet computer, a handheld personal data assistant, a smartphone, smart glasses, a smart wristwatch, a digital camera, a smart card incorporating a processor component, a body-worn computing device incorporated into clothing, a computing device integrated into a vehicle (e.g., a car, a bicycle, a wheelchair, etc.), a server, a cluster of servers, a server farm, etc.

As depicted, these computing devices 100, 200, 400 and 800 exchange signals implementing and/or supporting various forms of wireless communications. Among at least the computing devices 100, 200, 400 and/or 800, such exchanges may occur through the networks 199, 299 and/or 699 to exchange player data 435 and/or playing piece data 837. However, one or more of these computing devices may exchange other data entirely unrelated to game play with each other and/or with still other computing devices (not shown) via one or more of the networks 199, 299 and 699. In various embodiments, at least the networks 199 and/or 299 may be a single network possibly limited to extending within a single building or other relatively limited area, a combination of connected networks possibly extending a considerable distance, and/or may include the Internet. Thus, at least the networks 199 and/or 299 may be based on any of a variety (or combination) of communications technologies by which signals may be exchanged, including without limitation, wired technologies employing electrically and/or optically conductive cabling, and wireless technologies employing infrared, radio frequency or other forms of wireless transmission.

In various embodiments, the collection device may incorporate one or more of a processor component 150, a storage 160, controls 120, a display 180 and an interface 190 to couple the collection device 100 to one or more of the AP devices 200 via the network 199. The storage 160 stores one or more of a control routine 140, AP data 132, paring data 136, the player data 435 and the playing piece data 837. In various embodiments, each of the AP devices 200 may incorporate an interface 290 accompanied by an antenna 291 to enable reception of the player data 435 and/or the playing piece data 837 from the player device(s) 400 and/or the playing piece device 800 via the longer range wireless network 299.

The control routine 140 may incorporate a sequence of instructions operative on the processor component 150 to implement logic to perform various functions. In executing the control routine 140, the processor component 150 may operate one or more of the AP devices 200 to cooperate with the playing piece device 800 and/or the player device(s) 400 to form the longer range wireless network 299. In so doing, the processor component 150 may operate one or more of the AP devices 200 to engage in a pairing process with the playing piece device 800 and/or the player device(s) 400 to exchange security credentials. This may enable the AP device(s) 200 to recognize the playing piece device 800 and/or the player device(s) 400 as authorized participants in the longer range wireless network 299 from which to receive the player data 435 and/or the playing piece data 837. Correspondingly, this may enable the playing piece device 800 and/or the player device(s) 400 to recognize the AP device(s) 200 as authorized participant(s) in the network 299 to which the player data 435 and/or the playing piece data 837 may be transmitted. Alternatively or additionally, such a pairing procedure may entail implementing encryption or other security measures on the network 299.

During such a pairing process, the processor component 550 may generate the pairing data 136, which may include indications of identifiers and/or other information associated with the playing piece device 800 and/or the player device(s) 400. Alternatively, the devices 100, 200, 400 and 800 may be provided for use at a playing area as a kit or set of component for use in monitoring game play, and may be so provided having already been paired such that the pairing data 136 may have been pre-stored within the storage 160. Regardless of the exact manner in which the pairing data 136 is generated or otherwise provided, the processor component 150 may further provide the pairing data 136 and/or other data derived from the pairing data 136 to the playing piece device 800 and/or the player device(s) 400 to enable the playing piece device 800 and the player device(s) 400 to recognize each other as authorized participants in the shorter range wireless network 699. In essence, the processor component 150 may enable direct pairing of the playing piece device 800 to one or more of the player devices 400 to enable the formation of the shorter range wireless network 699.

Figure 2:
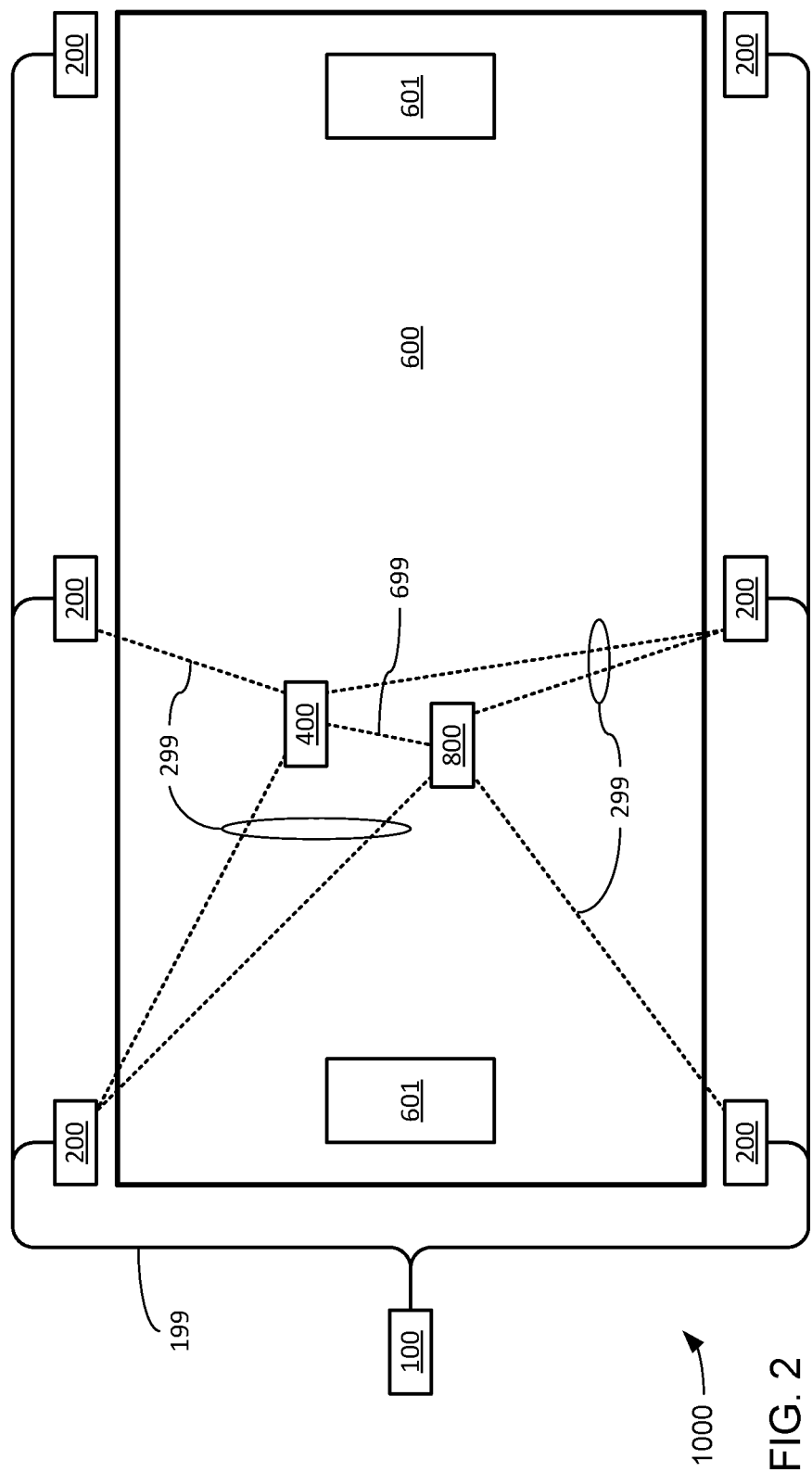
FIG. 2 illustrates an embodiment of positioning components of a game play monitoring system.

Also in executing the control routine 140, the processor component 150 may operate the AP device(s) 200 through the network 199 to receive the player data 435 and/or the playing piece data 837 via the network 299, and to relay one or both back to the collection device 100 via the network 199. FIG. 2 depicts an example of an installation of the game play monitoring system 1000 at a playing area 600. As depicted, the playing area 600 (e.g., a basketball or tennis court, a soccer field, etc.) may have a generally elongate rectangular shape with goal locations 601 (e.g., goal posts, a net-enclosed goal area, basket nets, etc.) at each end. However, this depiction of the playing area 600 is but an example, and the playing area 600 may take numerous other shapes and/or may include a differing quantity of goal locations 601 or no goal locations as appropriate for whatever type of sport is played there.

As also depicted, multiple AP devices 200 may be positioned about the playing area 600 so as to extend the area of coverage of the longer range wireless network 299 to the entirety of the playing area 600 such that the playing piece device 800 and the player device(s) 400 may engage in longer range communications with one or more of the AP devices 200 from any position to which each may be moved within the playing area 600. As also depicted, on occasions in which the playing piece device 800 is moved into relatively close proximity to one of the player devices 400, the playing piece device 800 and that player device 400 may momentarily form the shorter range wireless network 699. In some embodiments, what may differentiate the shorter range wireless network 699 and the type of lower power wireless communications on which it is based from the longer range wireless network 299 and the type of longer range wireless communications on which it is based may be the inability of the shorter range wireless network 699 to reach any of the AP devices 200 from anywhere within a substantial portion of (e.g., the majority of) the playing area 600.

More specifically, the shorter range wireless network 699 may be based on any of a variety of near-field communications (NFC) technology that may have a range of less than a meter. Alternatively or additionally, the shorter range wireless network 699 may be based on a communications technology often employed in creating personal area networks (PANs) that may have a range of less than five meters, which may be deemed appropriate to reach multiple devices carried by one person on different portions of their body and/or to reach objects positioned around a person within a cabin of a car or within a room of average size. By way of example, the shorter range wireless network may be based on the Bluetooth specification promulgated by the Bluetooth Special Interest Group of Kirkland, Wash. Thus, as the playing area 600 for many types of sports may be a dozen meters or more in at least one dimension, it may be unlikely that the shorter range wireless network 699 will be able to extend to cover the majority of the playing area 600. As familiar to those skilled in the art, such a limited range can be covered by a transmission generated with relatively little electric power.

In contrast, the longer range wireless network 299 may be based on any of a variety of wireless networking technologies that may have a range on the order of tens or hundreds of meters. By way of example, the longer range wireless network may be based on the Wi-Fi specification promulgated by the Wi-Fi Alliance of Austin, Tex. Thus, as the playing area 600 for many types of sports may be a dozen meters or more in at least one dimension, the longer range wireless network 299 may be based on a technology affording the ability to extend to cover the majority of the playing area 600. As familiar to those skilled in the art, such a greater range can be covered by a transmission generated with more electric power than needed to support the above-described transmissions of the shorter-range wireless network 699.

Returning to FIG. 1, in further executing the control routine 140, the processor component 150 may operate multiple ones of the AP devices 200 to transmit signals with known or otherwise configurable relative strengths that enable the player device(s) 400 and/or the playing piece device 800 to determine a current location within the playing area 600. By way of example, portions of the AP data 132, which may include indications of relative locations of each AP device 200 and/or relative strengths of transmissions made by each AP device 200, may be transmitted by the AP devices 200 to enable calculation of current locations relative to the AP devices 200 by the player device(s) 400 and/or the playing piece device 800. Alternatively or additionally, the processor component 150 may operate multiple ones of the AP devices 200 to determine the relative strengths with which each of those AP devices 200 receive signals from the playing piece device 800 and/or from one or more of the player devices 400. The processor component 150 may then employ indications of such relative signal strengths received from the AP devices 200 to determine locations of the playing piece device 800 and/or one or more of the player devices 400.

In embodiments of the collection device 100 that incorporate one or both of the controls 120 and the display 180, the processor component 150 may operate one or both to provide a user interface by which various features of the game play monitoring system 1000 may be configured. By way of example, the processor component 150 may monitor the controls 120 for an indication of manual operation of the controls 120 to trigger the performance of the earlier described pairing of the playing piece device 800 and/or the player devices 400 with each other and/or with the AP device(s) 200, at least partly under the control of the collection device 100. In performing such pairing, the processor component 150 may visually present indications on the display 180 of progress made and/or errors encountered in performing such pairing. By way of another example, the processor component 150 may monitor the controls 120 for an indication of manual operation of the controls 120 to provide indications of relative locations of multiple ones of the AP devices 200 relative to each other and/or relative to the playing area 600, and may include such indications in the AP data 132. Alternatively or additionally, the processor component 150 may monitor the controls 120 for an indication of manual operation of the controls 120 to configure aspects of the operation of the AP devices 200, including and not limited to, frequencies, encoding and/or relative strengths of signal transmissions by which the AP devices 200 participate in forming the longer range wireless network 299 and/or exchange other signals. Again, the processor component may visually present indications of progress and/or errors encountered in configuring such aspects of the operation of the AP devices 200 on the display 180 (if present) and/or may store indications of such aspects of operation as part of the AP data 132 stored within the storage 160.

In various embodiments, each of the one or more player devices 400 may incorporate one or more of a processor component 450, a storage 460, a power source 401, a proximity sensor 410, an interaction sensor 415, controls 420 and a display 480. Each of the player devices 400 may also incorporate an interface 490 accompanied by an antenna 491 to enable the player device 400 to engage in longer range communications with the AP device(s) 200 via the longer range wireless network 299 and/or engage in shorter range communications with the playing piece device 800 via the shorter range wireless network 699.

Figure 3B:
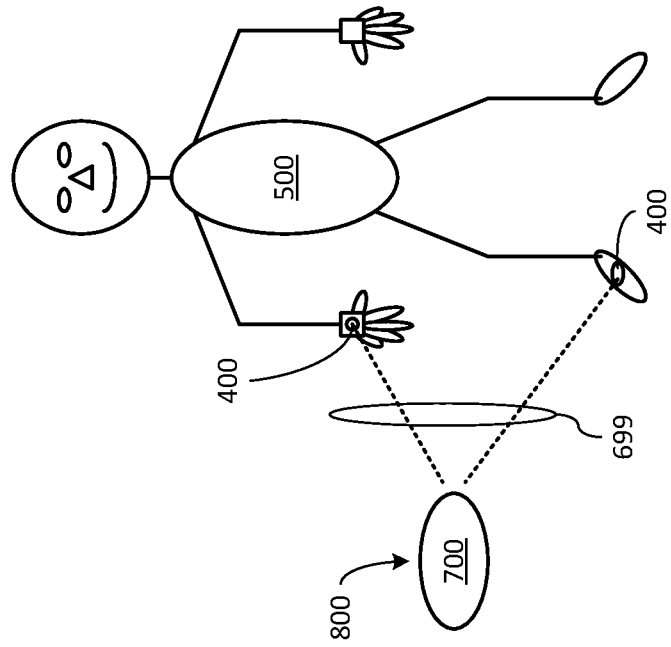
FIGS. 3A and 3B each illustrate embodiments of player devices and playing piece devices.
Figure 3A:
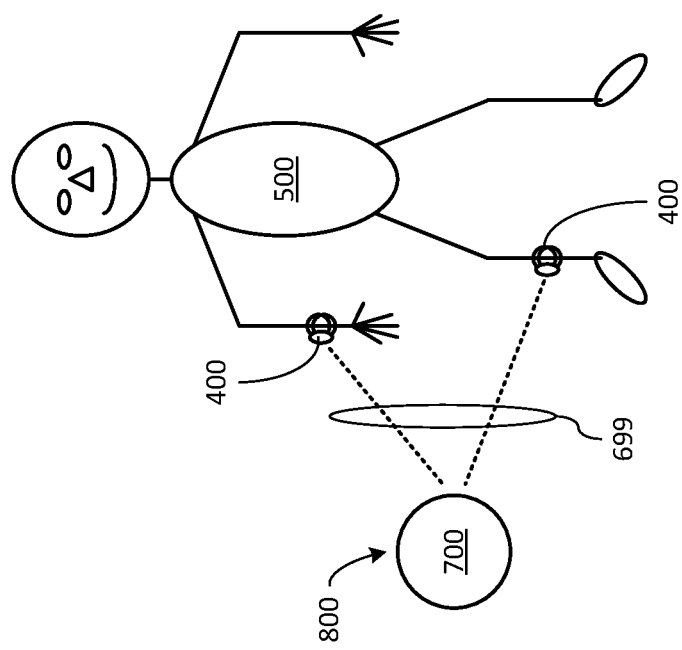

As previously discussed, a player's body 500 may carry at least one of the player devices 400 on a portion of their body 500 in any of a variety of ways. By way of example, and as depicted in FIG. 3A, a player's body 500 may wear one or more player devices 400 strapped onto different portions of their body in a manner akin to a clothing accessory, such as a watch or ankle bracelet as depicted. By way of another example, and as depicted in FIG. 3B, a player device 400 may be incorporated into one or more portions of a uniform and/or other piece of equipment associated with game play, such as a glove or shoe as depicted.

The control routine 440 may incorporate a sequence of instructions operative on the processor component 450 to implement logic to perform various functions. In executing the control routine 440, the processor component 450 may operate the interface 490 to cooperate with the AP devices 200 to form at least a portion of the longer range wireless network 299. In so doing, the processor component 450 may operate the interface 490 to exchange security credentials and/or the pairing data 136. This may enable the AP device(s) 200 to recognize the player device(s) 400 as authorized participants in the network 299 from which to receive the player data 435 and/or the playing piece data 837. Correspondingly, this may enable the player device(s) 400 to recognize the AP device(s) 200 as authorized participant(s) in the network 299 to which the player data 435 and/or the playing piece data 837 may be transmitted. Such an exchange of security credentials may also enable the use of encryption through the network 299.

As previously discussed, the collection device 100 may transmit at least portions of the pairing data 136 and/or other data derived from the pairing data 136 through the AP device(s) 200 to the playing piece device 800 and/or the player device(s) 400 to enable the playing piece device 800 and the player device(s) 400 to recognize each other as authorized participants on the shorter range wireless network 699. In essence, upon receiving the pairing data 136 or a derivative thereof, the processor component 450 may operate the interface 490 to engage in shorter range communications with the playing piece device 800 to become paired with the playing piece device 800 in support of forming the shorter range wireless network 699.

Also in executing the control routine 440, the processor component 450 of one of the player devices 400 carried on a portion of the player's body 500 may monitor the proximity sensor 410 for indications of the proximity sensor 410 detecting the playing piece 700 coming into relatively close proximity to the player's body 500. As familiar to those skilled in the art, statistics concerning when and/or how long a player's body 500 is within close proximity to the playing piece 700 may be significant in evaluating player performance and/or other aspects of game play. Thus, the processor component 450 may store indications of when the player's body 500 is in relatively close proximity to the playing piece 700 as part of the player data 435 stored within the storage 460.

The proximity sensor 410 may be based on any of a variety of technologies to detect when the playing piece 700 is in relatively close proximity to the player's body 500. In some embodiments, the playing piece 700 may incorporate one or more magnets emitting a magnetic field that the proximity sensor 410 may detect. As familiar to those skilled in the art, magnets of a size and/or weight amenable to being incorporated into a ball or puck are capable of generating a magnetic field of relatively limited range such that the playing piece 700 would need to be in relatively close proximity to the player's body 500 for the proximity sensor 410 to detect such a magnetic field. More specifically, the proximity sensor 410 may be made up of one or more magnetically-sensitive reed switches. In other embodiments, the playing piece 700 may emit a sound at a specific frequency and/or having other characteristics enabling the sound to be distinguished from other sounds deemed likely to be present within the playing area 600. The sound may be emitted by the playing piece 700 with a selected amplitude to enable the sound to be detected by the proximity sensor 410 within only the relatively close proximity More specifically, the playing piece 700 may emit a sound at a selected ultrasonic frequency (e.g., at a frequency that may be selected to be above the range of frequencies normally perceptible to human hearing), and the proximity sensor 410 may be made up of one or more microphones and/or other form of acoustic sensor that may be selected and/or configured to detect the sound at the selected ultrasonic frequency.

Alternatively or additionally, characteristics of the shorter range wireless network 699 may be employed in proximity detection. More specifically, the type of wireless communications on which the network 699 may be based may be selected to have a range that may be sufficiently short as to be usable as a basis on which to determine whether or not the playing piece 700 and the player's body 500 are in relatively close proximity to each other. In such embodiments, if the interface 490 is able to detect a transmission from the playing piece device 800 to form the shorter range wireless network 699 therebetween and/or to use the shorter range wireless network 699 to exchange data, then the processor component 450 may make the determination that the playing piece 700 is within relatively close proximity, and may store an indication to that effect as part of the player data 435 in the storage 460. In such embodiments, such use of the interface 490 by the processor component 450 as a proximity sensor to detect when the playing piece 700 is in relatively close proximity may be either in addition to or in lieu of incorporating the proximity sensor 410 to do so.

More generally, in some embodiments, a relatively close proximity may be defined by how far a player is able to reach with a hand or a foot of their body 500. Stated differently, and regardless of the technology or technique employed to detect proximity, the playing piece 700 may be said to be in relatively close proximity to a player's body 500 if that player is able to reach out and interact with the playing piece 700 with a hand or foot of their body.

In further executing the control routine 440, the processor component 450 of one of the player devices 400 carried on a portion of a player's body 500 may monitor the interaction sensor 415 for indications of the interaction sensor 415 detecting interaction between the player's body 500 and the playing piece 700. As familiar to those skilled in the art, statistics concerning interactions of a player's body 500 with the playing piece 700 are often significant in evaluating player performance and/or other aspects of game play. Thus, the processor component 440 may store indications of each detected interaction of the player's body 500 with the playing piece 700 as part of the player data 435 stored in the storage 460.

The interaction sensor 415 may be made up of one or more sensing components based on any of a variety of technologies. The one or more sensing components may detect interaction of the player's body 500 with the playing piece 700 in a direct manner in which the one or more sensing components of the interaction sensor 415 directly detect contact with a portion of the playing piece 700. This technique may be used in embodiments in which at least a portion of the interaction sensor 415 is incorporated into a portion of a uniform or other piece of equipment associated with game play where it is expected and/or deemed likely that the playing piece 700 will make contact with that portion of a uniform or other piece of equipment as a result of the player interacting with the playing piece 700 with a portion of their body 500. By way of example, and referring again to FIG. 3B where player device(s) 400 may be incorporated into gloves, shoes, etc. worn on the player's body 500, and where those gloves, shoes, etc. are deemed likely to come into contact with the playing piece 700 as the player kicks, dribbles, throws, catches, etc. the playing piece 700, detecting interaction between the player's body 500 and the playing piece 700 may entail sensing of contact with the gloves, shoes, etc. In such an example, the interaction sensor 415 may be made up of contact detection and/or shock force detection sensors positioned on or integrated into exterior surface to detect touch and/or impact interactions with the playing piece 700.

Alternatively, the one or more sensing components of the interaction sensor 415 may detect interaction of the player's body 500 with the playing piece 700 in an indirect manner in which the one or more sensing components of the interaction sensor 415 detect movement and/or other events associated with portion(s) of the body 500 of the player that may be deemed consistent with interaction with the playing piece 700. This technique may be used in embodiments in which at least a portion of the interaction sensor 415 is worn on a portion of the body 500 of the player where contact with the playing piece 700 is deemed less likely or unlikely to occur, such as a portion of an arm or a leg that is away from the corresponding hand or foot in a type of sport in which interaction with the playing piece 700 is expected to entail contact with a hand or a foot. Thus, instead of being made up of sensing components selected to directly sense contact, the interaction sensor 415 may be made up of sensing component(s) that detect direction of movement and/or acceleration of a body portion, a shock force transmitted along muscle and/or bone of a body portion, etc. By way of example, and referring again to FIG. 3A where player device(s) 400 may be strapped to an arm or a leg of the player's body 500, detecting interaction between the player's body 500 and the playing piece 700 may entail sensing a movement of an arm or a leg that may be deemed consistent with the player kicking, catching, throwing, dribbling, etc. the playing piece 700. Alternatively or additionally in this example, detecting such interaction may entail sensing a vibration or shock force transmitted along muscles and/or bones of an arm or a leg that are deemed likely to be an indication of an impact with the playing piece 700 that is associated with interaction with the playing piece 700.

The power source 401 may be a battery or other type of source of electric power of relatively limited capacity. By way of example, the power source 801 may be a type of generator that generates electric power from physical movement of the player's body 500 or thermal energy output by the player's body 500, either of which may fluctuate greatly with the degree to which the player's body 500 may be physically active at any given time. Depending on the rate of consumption of electric power required to monitor the interaction sensor 415, the processor component 450 may seek to conserve the electric power provided by the power source 401 by restricting the provision of electric power to monitor the interaction sensor 415 until the proximity sensor 410 detects that the playing piece 700 is within relatively close proximity to the player's body 500.

As has been discussed, the processor component 450 may alternatively or additionally conserve the electric power provided by the power source 401 by conditioning operation of the interface 490 to at least engage in longer range communications via the longer range wireless network 299 on whether or not the playing piece 700 is at least detected as being in relatively close proximity to the player's body 500. In some embodiments, the processor component 450 may further condition such operation of the interface 490 on whether or not interaction of the player's body 500 with the playing piece 700 has also been detected. Thus, the processor component 450 may monitor the proximity sensor 410 on a relatively uninterrupted basis, but may restrict the provision of electric power from the power source 401 to operate the interaction sensor 415 to detect interaction with the playing piece 700 and/or to operate the interface 490 to engage in at least longer range communications via the longer range wireless network 299 until the playing piece 700 is detected as being in relatively close proximity. For example, the processor component 450 may monitor the proximity sensor 410, and then enable use of electric power to operate the interaction sensor 415 when the playing piece 700 is detected as being in relatively close proximity. The processor component 450 may then await detection of interaction with the playing piece 700 before enabling the use of electric power to operate the interface 490 to engage in longer range communications via the longer range wireless network 299. Alternatively, the processor component 450 may monitor both the proximity sensor 410 and the interaction sensor 415 for indications of the playing piece 700 being in relatively close proximity and indications of interaction between the player's body 500 and the playing piece 700, and may enable the use of electric power from the power source 401 to operate the interface 490 to engage in longer range communications only when both have been detected.

It should be noted that after the use of electric power from the power source to operate at least the interface 490 to at least engage in longer range communications has been enabled, it may remain enabled for a predetermined period of time following the last detected interaction with the playing piece 700 as long as the playing piece 700 continues to be detected as being in relatively close proximity. The length of the predetermined period of time may be selected to allow for up to a particular amount of time that is deemed likely to pass between each detectable instance of interaction with the playing piece 700 that a player may have while the player's body 500 is interacting with the playing piece 700. Stated differently, while the playing piece 700 may remain within a relatively close proximity to a player's body 500 on an uninterrupted basis, the player's body 500 may not be in contact with the playing piece 700 on an uninterrupted basis. Instead, as recognizable to those skilled in the art, each contact made with the playing piece 700 to dribble it, kick it a short distance (e.g., between the two feet of a player's body 500 while moving across a field) of the playing piece 700 is an instance of an interaction with the playing piece 700 such that, generally, interaction by a player's body 500 with the playing piece 700 may be a series of individual interactions. Thus, as long as the playing piece 700 continues to be detected as in relatively close proximity to the player's body 500, and as long as the amount of time that passes between detected instances of interaction does not exceed the predetermined period of time, then the processor component 450 may continue to enable the use of electric power to operate the interface 490 to at least engage in longer range communications.

As previously discussed, operation of the interface 490 to engage in longer range communications via the longer range wireless network 299 may consume electric power at a considerably greater rate than operation of the interface 490 to engage in shorter range communications via the shorter range wireless network 699. Thus, in some embodiments, the interface 490 may be operated by the processor component 450 on a relatively uninterrupted basis to monitor for transmissions from the playing piece device 800 attempting to form the shorter range wireless network 699 as a mechanism to detect whether the playing piece 700 is in relatively close proximity. In some embodiments, the interface 490 may be made up of more than one wireless communications transceiver, with one selected and/or configured to engage in shorter range communications via the shorter range wireless network 699, and with another selected and/or configured to engage in longer range communications via the longer range wireless network 299. Thus, selectively enabling operation of the interface 490 to monitor for signals from the playing piece device 800 attempting to form the shorter range wireless network 699 while also disallowing the use of electric power to operate the interface 490 to engage in longer range communications may entail enabling the use of electric power by one wireless communications transceiver of the interface 490 while disabling use of electric power to another wireless communications transceiver of the interface 490. However, in other embodiments in which the player device 400 incorporates the proximity sensor 410 and the interface 490 is not operated to perform such proximity detection, the provision of electric power to wireless communications transceivers for both shorter range and longer range wireless communications may be disabled by the processor component 450 at least until the proximity sensor 410 has detected the playing piece as being in relatively close proximity.

With the use of electric power to operate the interface 490 to engage in longer range communications via the longer range wireless network 299 enabled due at least to the detection of the playing piece 700 as being at least in relatively close proximity, the processor component 450 may operate the interface 490 to transmit portions of the player data 435 to the collection device 100 via the network 299 and one or more of the AP devices 200. Further, the processor component 450 may additionally operate the interface 490 to receive the playing piece data 837 from the playing piece device 800 via the shorter range wireless network 699. The processor component 450 may temporarily store the playing piece data 837 within the storage 460 to buffer the playing piece data 837 ahead of operating the interface 490 to transmit portions of the playing piece data 837 to the collection device 100 along with the player data 435. Stated differently, the processor component 450 may operate the interface 490 to relay portions of the playing piece data 837 received from the playing piece device 800 via the shorter range wireless network 699 to the collection device 100 via the longer range wireless network 299 and at least one of the AP devices 200.

In still further executing the control routine 440, and at times when the use of electric power to operate the interface 490 to engage in longer range communications via the longer range wireless network 229 is enabled, the processor component 450 may analyze signals received from more than one of the AP devices 200 to determine the current location of the player device 400 relative to the AP devices 200. More specifically, the processor component 450 may operate the interface 490 to determine relative strengths of signals received from more than one of the AP devices 200 to determine relative distances of the player device 400 from each of those AP device 200. The analyzed signals from those AP devices 200 may be among the signals received from those AP devices 200 as part of engaging in longer range wireless communications through the longer range wireless network 299. As part of determining relative distances from each of those AP devices 200, the processor component 450 may operate the interface 490 to receive the AP data 132 from the collection device 100 through the longer range wireless network 299 and the AP devices 200. As previously discussed, the AP data 132 may include indications of the relative strengths of transmissions from each of the AP devices 200.

The processor component 450 may further operate the interface 490 to transmit an indication of the current location of the player device 400 to the playing piece device 800 via the shorter range wireless network 699 at a time when the playing piece 700 is at least within a relatively close proximity to the player device 400. Such an indication transmitted to the playing piece device 800 may include an indication of the current location of the player device 400 relative to the AP devices 200 as derived by the processor component 450 from the analysis of the relative strengths of signals received from the AP devices 200. Alternatively, such an indication transmitted to the playing piece device 800 may include an indication of the relative strengths of signals received from the AP devices 200 as determined by the processor component 450. It should be noted that although the indication may be of the current location of the player device 400, the relatively close proximity of the playing piece device 800 at the time of the transmission of such an indication means that the indication is effectively also of the location of the playing piece device 800 within an amount of error no greater than the maximum distance at which the proximity sensor 410 may detect that the playing piece 700 is within a relatively close proximity to the player's body 500.

In embodiments of the player device 400 that incorporate one or both of the controls 420 and the display 480, the processor component 450 may operate one or both to provide a user interface by which various features of the operation of at least the player device 400 may be configured. By way of example, the processor component 450 may monitor the controls 420 for an indication of manual operation of the controls 420 to trigger the performance of the above described pairing of the player device 400 with the playing piece device 800 and/or with the AP device(s) 200. In performing such pairing, the processor component 450 may visually present indications on the display 480 (if present) of progress made and/or errors encountered in performing such pairing.

In various embodiments, the playing piece device 800 may incorporate one or more of a processor component 850, a storage 860, a power source 801, a proximity signal emitter 870, an interaction sensor 815 and controls 820. The playing piece device 800 may also incorporate an interface 890 accompanied by an antenna 891 to enable the playing piece device 800 to engage in longer range communications with the AP device(s) 200 via the longer range wireless network 299 and/or engage in shorter range communications with the player devices 400 via the shorter range wireless network 699. As previously discussed, the playing piece device 800 may be incorporated into the playing piece 700. Again, the playing piece 700 may be fabricated to incorporate the playing piece device 800 or may be fabricated with the playing piece device 800 already in place therein.

The control routine 840 may incorporate a sequence of instructions operative on the processor component 850 to implement logic to perform various functions. In executing the control routine 840, the processor component 850 may operate the interface 890 to cooperate with the AP devices 200 to form at least a portion of the longer range wireless network 299 (e.g., perform a pairing procedure). In so doing, the processor component 850 may operate the interface 890 to exchange security credentials and/or the pairing data 136. This may enable the AP device(s) 200 to recognize the playing piece device 800 as an authorized participant in the network 299 from which to receive the playing piece data 837 at times when the playing piece device 800 does not relay portions of the playing piece data 837 through a player device 400. Correspondingly, this may enable the playing piece device 800 to recognize the AP device(s) 200 as authorized participant(s) in the network 299 to which portions of the playing piece data 837 may be transmitted. Such an exchange of security credentials may also enable the use of encryption through the network 299.

As previously discussed, the collection device 100 may transmit at least portions of the pairing data 136 and/or other data derived from the pairing data 136 through the AP device(s) 200 to the playing piece device 800 and/or the player device(s) 400 to enable the playing piece device 800 and the player device(s) 400 to recognize each other as authorized participants on the shorter range wireless network 699. In essence, upon receiving the pairing data 136 or a derivative thereof, the processor component 850 may operate the interface 890 to engage in shorter range communications with one or more player devices 400 to become paired with those player devices 400 in support of forming the shorter range wireless network 699.

As previously discussed, any of a variety of technologies may be employed to enable the proximity sensor 410 of a player device 400 to detect whether the playing piece 700 is in relatively close proximity to a player's body 500 who carries the player device 400. As also previously discussed in an example, the proximity signal emitter 870 may be made up of one or magnets emitting a magnetic field for the proximity sensor 410 to detect. As also previously discussed in another example, the proximity signal emitter 870 may be made up of one or more acoustic drivers (e.g., one or more piezo elements, electromagnetic cone speakers, electrostatic speakers, etc.), and the processor component 850 may operate the one or more acoustic drivers to acoustically emit a sound at an ultrasonic or other frequency for the proximity sensor 410 to detect.

Alternatively or additionally, characteristics of the shorter range wireless network 699 may be employed in proximity detection. Again, the type of wireless communications on which the network 699 may be based may be selected to have a range of transmission that may be sufficiently short as to be usable as a basis on which to determine whether or not the playing piece 700 and the player's body 500 are in relatively close proximity to each other. In such embodiments, the processor component 850 may operate the interface 890 to recurringly emit radio frequency signals of a frequency selected to conform to the type shorter range communications chosen to implement the shorter range wireless network 699. More specifically, at times when the playing piece device 800 is not already engaged in shorter range wireless communications with a player device 400 via the shorter range wireless network 699, the processor component 850 may operate the interface 890 to recurringly transmit signals querying for the presence of any player devices 400 within the relatively close proximity of the playing piece device 800. One or more of the player devices 400 may employ such recurring transmissions from the playing piece device 800 to detect that the playing piece 700 is within the relatively close proximity to a player's body 500.

In further executing the control routine 840, the processor component 850 of the playing piece device 800 may monitor the interaction sensor 815 for indications of the interaction sensor 815 detecting interaction between the playing piece 700 and a player's body 500. Again, statistics concerning interactions of players' bodies 500 with the playing piece 700 are often significant in analyzing aspects of game play. Thus, the processor component 840 may store indications of each detected interaction with a player's body 500 as part of the playing piece data 837.

The interaction sensor 815 may be made up of one or more sensing components based on any of a variety of technologies. The one or more sensing components may detect interaction of the playing piece 700 with a player's body 500 in a direct manner in which the one or more sensing components of the interaction sensor 815 directly detects contact with the playing piece 700. Sensing components of the interaction sensor 815 that are able to directly sense physical contact with exterior surfaces of the playing piece 700 may be positioned on or integrated into those exterior surfaces (e.g., resistive, capacitive or other forms of contact sensing components). The type of technology employed by the interaction sensor 815 may be selected to detect contacts falling within a selected range of magnitudes and/or other characteristics of force applied.

Alternatively, the one or more sensing components may detect interaction of the playing piece 700 with a player's body 500 in an indirect manner in which the one or more sensing components of the interaction sensor 415 detect movement and/or other events associated with the playing piece 700 being carried, kicked, thrown, caught, dribbled or otherwise caused to move in various ways by interaction with a player's body 500. Motion sensing components of the interaction sensor 415 (e.g., accelerometers, gyroscopes, shock force sensors, etc.) may be incorporated into the playing piece 700 to detect movement and/or changes in movement that may be deemed consistent with a player's body 500 interacting with the playing piece 700.

The power source 801 may be a battery or other type of source of electric power of relatively limited capacity. By way of example, the power source 801 may be a type of generator that generates electric power from physical movement of the playing piece 700, which may fluctuate greatly with the degree to which the playing piece 700 is interacted with.

As has been discussed, the processor component 850 may conserve the electric power provided by the power source 801 by conditioning the use of electric power from the power source to operate the interface 890 to at least engage in longer range communications via the longer range wireless network 299 on a determination of whether the playing piece 700 is likely to be in close proximity to the body or bodies 500 of one or more players based on detected interactions with the playing piece 700. More precisely, the interaction sensor 815 may include one or more motion sensors (e.g., accelerometers, gyroscopes, shock force sensors, etc.) able to sense movement and changes in movement that may be consistent with ongoing interactions with the playing piece 700 by the body or bodies 500 of one or more players such that it may be determined that the playing piece 700 is being interacted with in a manner that it is likely to remain in relatively close proximity to one or more players' bodies 500. Further, the same motion sensors may also be able to sense relatively lengthy and uninterrupted movement that may be more consistent with the playing piece 700 being subjected to a type of interaction in which it is kicked or thrown for a considerable distance such that it has likely left the proximity of the one or more players who caused the playing piece 700 to move in such a manner such that it may be determined that the playing piece 700 is currently not in relatively close proximity to any player's body 500.

More generally, in some embodiments, a relatively lengthy movement consistent with the playing piece 700 no longer being in close proximity to any player's body 500 may be defined by a magnitude of force applied to the playing piece 700 during an interaction that imparts movement to the playing piece 700 that remains uninterrupted for a period time long enough that the playing piece 700 has at least moved away from being in relatively close proximity to the body or bodies 500 with which interaction imparted the movement. By way of example, if an interaction is detected that applies an amount of force to the playing piece 700 that exceeds a threshold level of force, and if the movement imparted to the playing piece 700 is allowed to continue for an amount of time that exceeds a threshold amount of time, then the processor component 850 may determine that the playing piece 700 has moved a sufficient length of distance that it is at least no longer in relatively close proximity to the body 500 of the player who applied that force, and that the playing piece 700 is likely no longer in close proximity to any other players' bodies 500.

The processor component 850 may use indications of which type of movement is detected by the interaction sensor 815 and corresponding determinations about proximity to players' bodies 500 to determine whether to use electric power from the power source 801 at a lesser rate to operate the interface 890 to attempt to engage in shorter range communications via the shorter range wireless network 699 or to use that electric power at a greater rate to engage in longer range communications via the longer range wireless network 299. More precisely, while the interaction sensor 815 detects physical interaction and/or movement of the playing piece 700 that is deemed consistent with interaction with players 500 that keeps the playing piece 700 in relatively close proximity to at least one player 500, the processor component 850 may use the lesser amount of electric power from the power source 801 to attempt to use and to maintain shorter range communications with one or more player devices 400 carried on a portion of the body or bodies 500 of at least one player. If successful in forming the shorter range wireless network 699 with at least one player device 400, the processor component 850 may then transmit portions of the playing piece data 837 to the at least one player device 400 to be relayed thereby to the collection device 100 via the longer range wireless network 299 and one or more AP devices 200. However, if the interaction sensor 815 detects interaction and/or movement of the playing piece 700 that is deemed consistent with an interaction leading to a lengthy and uninterrupted movement (e.g., being thrown or kicked a considerable distance), then the processor component 850 may cease to use the lesser amount of electric power to attempt to use shorter range communications. Instead, the processor component 850 may use the greater amount of electric power needed to engage in longer range communications with one or more of the AP devices 200 to transmit portions of the playing piece data 837 to the collection device 100 via the longer range wireless network 299 and the one or more AP devices 200.

Figure 4:
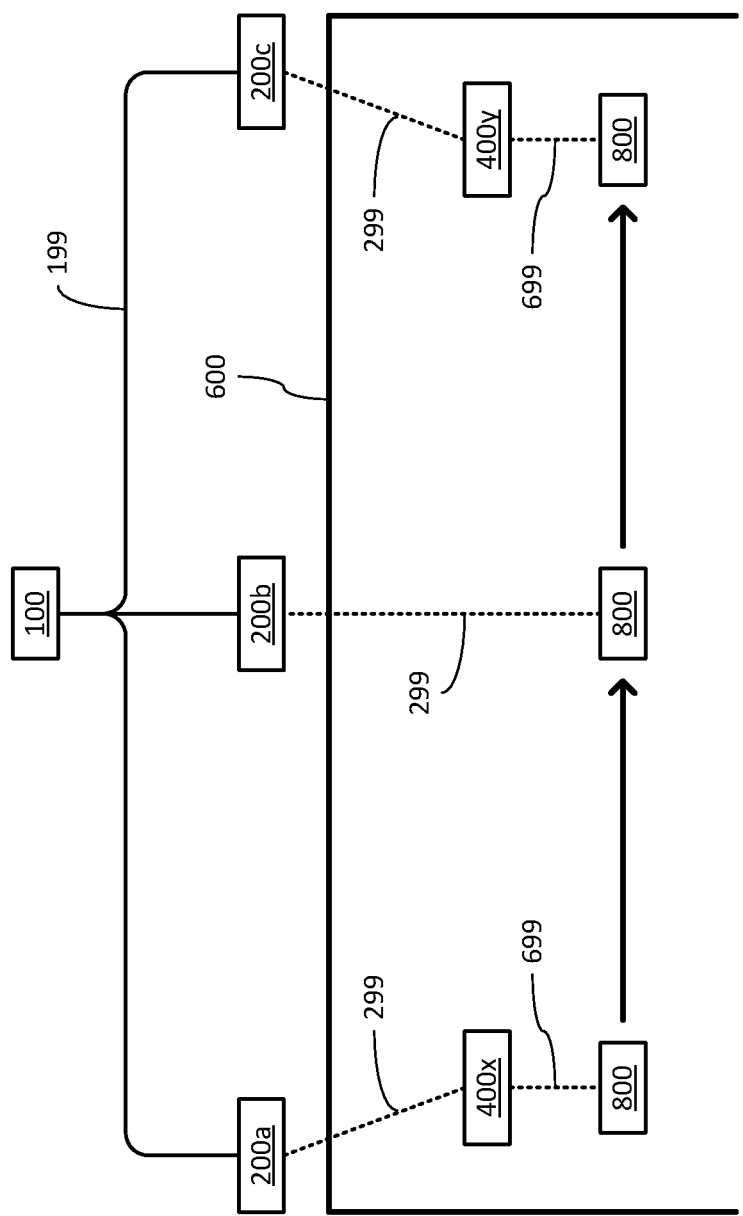
FIG. 4 illustrates an embodiment of transitions in types of communications used by a playing piece device.

FIG. 4 illustrates an example of transitions that may be effected by the processor component 850 between the use of shorter range and longer range communications as the playing piece 700 is moved a lengthy distance as a result of interactions with players 500 from one portion of a playing area 600 to another. More specifically, the playing piece 700 incorporating an example embodiment of the playing piece device 800 may initially be in relatively close proximity to the body 500x of a player on which is carried a player device 400x that engages in longer range communications with an AP device 200a via a portion of the longer range wireless network 299. As a result of interactions between the player 500x and the playing piece 700, the playing piece device 800 forms the shorter range wireless network 699 with the player device 400x, thereby enabling the playing piece device 800 to transmit portions of playing piece data 837 to the collection device 100 by relaying that data through the player device 400x. Due to the shorter range wireless network 699 formed between the playing piece device 800 and the player device 400x, the playing piece device 800 is able to use a lesser amount of electric power to transmit that data to the player device 400x, and rely on the player device 400x to use the greater amount of electric power required to engage in longer range communications via the longer range wireless network 299 to relay that data.

However, after some period of time being interacted by at least the player 500x in a manner resulting in various instances of movement of relatively short distance, the player 500x may throw or kick the playing piece 700 towards another player 500y at another portion of the playing area 600 that is a considerably lengthy distance away. As a result of detecting interaction leading to the application of force exceeding a threshold of force and leading to movement that may continue for an amount of time exceeding a threshold of time, the processor component 850 may determine that the playing piece 700 is no longer in close proximity to any player, and may enable the use of the greater amount of electric power required to engage in longer range communications. In so doing, the playing piece device 800 may engage in longer range communications via another portion of the longer range wireless network 299 with another AP device 200b. As the detected relatively lengthy movement continues, the playing piece device 800 may transmit more data to the collection device 100 via the longer range wireless network 299 and the AP device 200b.

Then, the relatively lengthy movement may end as the playing piece 700 reaches the player 500y and is interacted with by the player 500y such that a new force is applied that changes the movement of the playing piece 700. In response to detecting physical interaction and/or movement of the playing piece 700 that may be deemed consistent with interaction with a player (e.g., the player 500y), the playing piece device 800 may again attempt to conserve electric power by ceasing to use the greater amount of electric power required to engage in longer range communications. Instead, the playing piece device 80 may again use the lesser amount of electric power required to again attempt and maintain shorter range communications, this time with the player device 400y carried on a portion of the body of the player 500y and engaged in longer range communications with an AP device 200c via another portion of the longer range wireless network 299.

In still further executing the control routine 840, and at times of using the greater amount of electric power to engage in longer range communications via the longer range wireless network 299, the processor component 850 may operate the interface 890 to determine the relative strengths of signals received from more than one AP device 200 to at least distinguish the current location of the playing piece 700 from other locations at least within the playing area 600. It should be noted that, the processor component 850 may make no effort to determine how relative strengths of signals received from the more than one AP devices 200 correlate to locations within the playing area 600. Instead, the processor component 850 may simply use those differences in relative strengths to simply distinguish between different locations. The processor component 850 may also operate the interface 890 to determine a level of quality of the longer range communications that are possible at the current location within the playing area 600, and may store indications of correlations between locations distinguished by differences in relative strengths of signals and levels of quality of longer range communications that are possible at those locations as part of the correlation data 836. The range of detected quality of longer range communications may include a sufficiently poor degree of quality that considerable electric power is wasted in repeatedly retransmitting data before it is successfully received and/or may include a sufficiently high degree of quality that higher data rates may be used enabling data to be transmitted in less time such that less electric power may be needed.

As an alternative, the processor component 850 may operate the interface 890 to receive the AP data 132 from the collection device 100, either directly through the longer range wireless network 299 and the AP devices 200, or indirectly as relayed through a player device 400. The processor component 850 may then use indications of relative strengths of transmission of signals of each AP device 200 and/or indications of relative positions of the AP devices 200 within the AP data 132 to correlate detected differences in strengths of signals received from the AP devices 200 to locations within the playing area 600. The processor component 850 may then store indications of correlations between locations as determined through use of the AP data 132 and levels of quality of longer range communications that are possible at those locations as part of the correlation data 836.

As another alternative, and at times of using the lesser amount of electric power to engage in shorter range communications via the shorter range wireless network 699, the processor component 850 may operate the interface 890 to receive indications from a player device 400 of the current location and/or the relative strengths of signals received by that player device 400 from one or more of the AP devices 200 at that location. The processor component 850 may further operate the interface 890 to receive indications of quality of longer range communications detected by that player device 400 from that location, and processor component 850 may store indications of correlations of locations as determined by that player device 400 and the quality of longer range communications that are determined by that player device 400 to be possible at those locations as part of the correlation data 836.

Regardless of the manner in which the processor component 850 acquires the indications that it stores in the correlation data 136 between locations and quality of longer range communications that are possible at those locations, the processor component 850 may employ the correlation data 136 as an additional factor in determining whether to engage in shorter range or longer range communications. By way of example, where the interaction sensor 815 detects movement consistent with the playing piece 700 being kicked or thrown a considerable distance such that it may be deemed unlikely that there are any players 500 in close proximity, the playing piece 700 may refrain from using the greater amount of energy required to engage in longer range communications as a result of determining that the current location of the playing piece 700 or its location just prior to the current movement was a location associated with a relatively poor quality of longer range communications.

Returning to FIG. 1, in embodiments of the playing piece device 800 that incorporate the controls 820, the processor component 850 may operate the controls 820 to provide a user interface by which various features of the operation of at least the playing piece device 800 may be configured. By way of example, the processor component 850 may monitor the controls 820 for an indication of manual operation of the controls 820 to trigger the performance of the above described pairing of the playing piece device 800 with the player device(s) 400 and/or with the AP device(s) 200.

In various embodiments, each of the processor components 150, 450 and 850 may include any of a wide variety of commercially available processors. Further, one or more of these processor components may include multiple processors, a multi-threaded processor, a multi-core processor (whether the multiple cores coexist on the same or separate dies), and/or a multi-processor architecture of some other variety by which multiple physically separate processors are in some way linked.

In various embodiments, each of the storages 160, 460 and 860 may be based on any of a wide variety of information storage technologies, possibly including volatile technologies requiring the uninterrupted provision of electric power, and possibly including technologies entailing the use of machine-readable storage media that may or may not be removable. Thus, each of these storages may include any of a wide variety of types (or combination of types) of storage device, including without limitation, read-only memory (ROM), random-access memory (RAM), dynamic RAM (DRAM), Double-Data-Rate DRAM (DDR-DRAM), synchronous DRAM (SDRAM), static RAM (SRAM), programmable ROM (PROM), erasable programmable ROM (EPROM), electrically erasable programmable ROM (EEPROM), flash memory, polymer memory (e.g., ferroelectric polymer memory), ovonic memory, phase change or ferroelectric memory, silicon-oxide-nitride-oxide-silicon (SONOS) memory, magnetic or optical cards, one or more individual ferromagnetic disk drives, or a plurality of storage devices organized into one or more arrays (e.g., multiple ferromagnetic disk drives organized into a Redundant Array of Independent Disks array, or RAID array). It should be noted that although each of these storages is depicted as a single block, one or more of these may include multiple storage devices that may be based on differing storage technologies. Thus, for example, one or more of each of these depicted storages may represent a combination of an optical drive or flash memory card reader by which programs and/or data may be stored and conveyed on some form of machine-readable storage media, a ferromagnetic disk drive to store programs and/or data locally for a relatively extended period, and one or more volatile solid state memory devices enabling relatively quick access to programs and/or data (e.g., SRAM or DRAM). It should also be noted that each of these storages may be made up of multiple storage components based on identical storage technology, but which may be maintained separately as a result of specialization in use (e.g., some DRAM devices employed as a main storage while other DRAM devices employed as a distinct frame buffer of a graphics controller).

In various embodiments, at least a portion of each of the interfaces 190, 290, 490 and 890 may employ any of a wide variety of signaling technologies enabling these computing devices to be coupled to other devices as has been described. Each of these interfaces includes circuitry providing at least some of the requisite functionality to enable such coupling. However, each of these interfaces may also be at least partially implemented with sequences of instructions executed by corresponding ones of the processor components (e.g., to implement a protocol stack or other features). Where electrically and/or optically conductive cabling is employed, these interfaces may employ signaling and/or protocols conforming to any of a variety of industry standards, including without limitation, RS-232C, RS-422, USB, Ethernet (IEEE-802.3) or IEEE-1394. Where the use of wireless signal transmission is entailed, these interfaces may employ signaling and/or protocols conforming to any of a variety of industry standards, including without limitation, IEEE 802.11a, 802.11b, 802.11g, 802.16, 802.20 (commonly referred to as "Mobile Broadband Wireless Access"); Bluetooth; ZigBee; or a cellular radiotelephone service such as GSM with General Packet Radio Service (GSM/GPRS), CDMA/1×RTT, Enhanced Data Rates for Global Evolution (EDGE), Evolution Data Only/Optimized (EV-DO), Evolution For Data and Voice (EV-DV), High Speed Downlink Packet Access (HSDPA), High Speed Uplink Packet Access (HSUPA), 4G LTE, etc.

Figure 5:
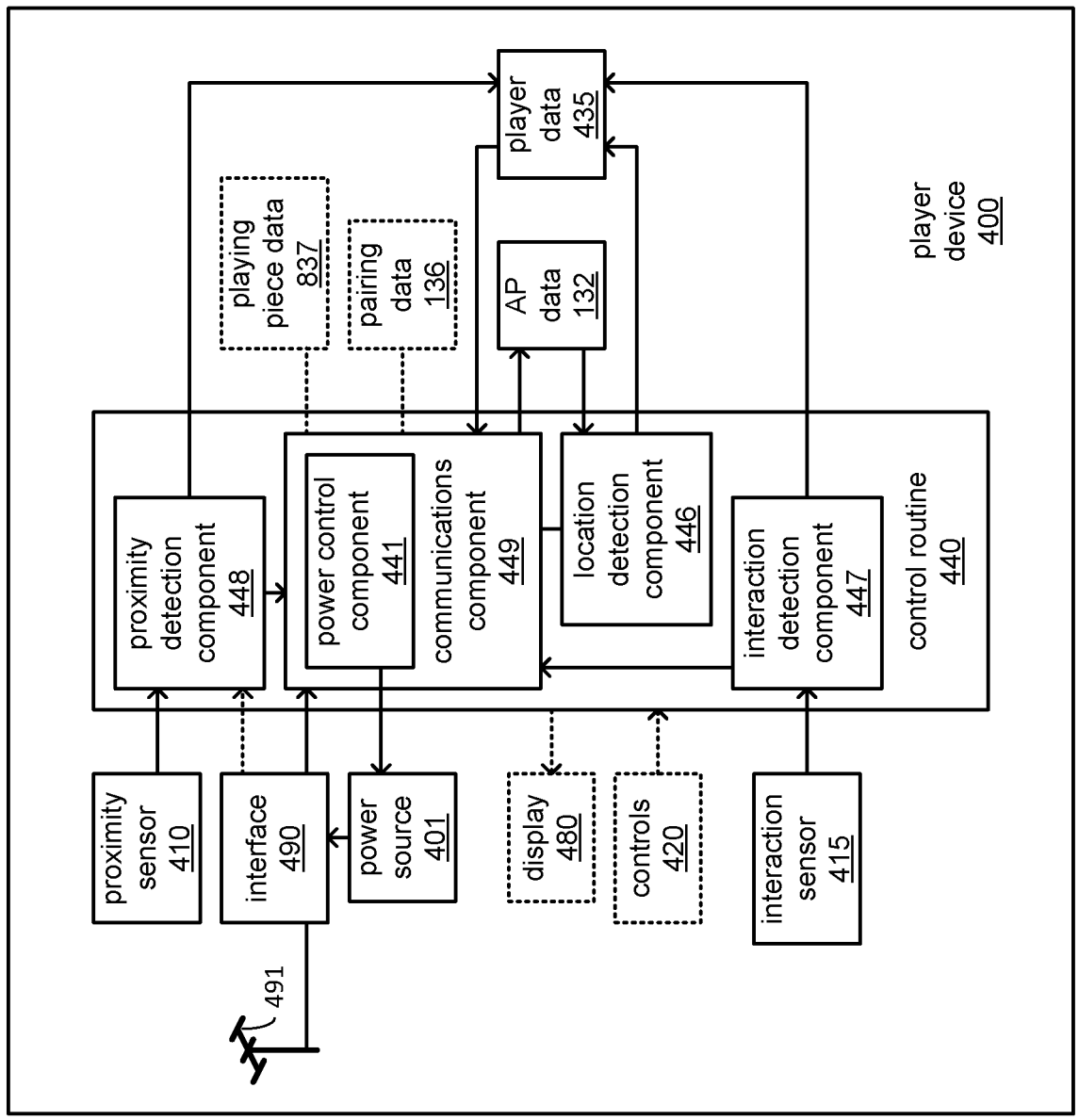
FIGS. 5 and 6 each illustrate a portion of an embodiment.
Figure 6:
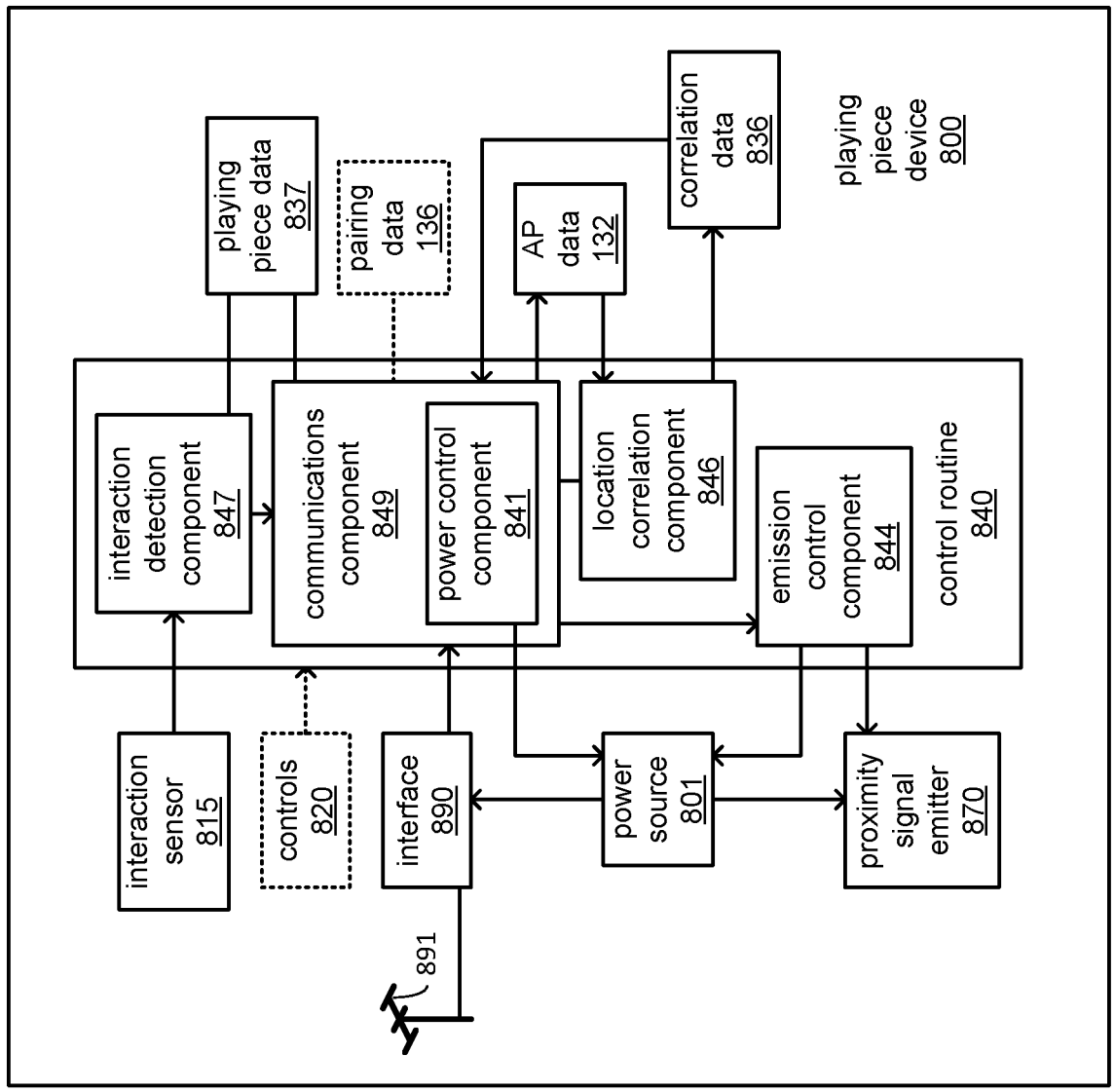

FIGS. 5 and 6 each illustrate a block diagram of a portion of an embodiment of the game play monitoring system 1000 of FIG. 1 in greater detail. More specifically, FIG. 5 depicts aspects of the operating environment of a player device 400 in which the processor component 450, in executing the control routine 440, collects and transmits portions of the player data 435 to the collection device 100 along portions of the playing piece data 837 received from the playing piece device 800. FIG. 6 depicts aspects of the operating environment of the playing piece device 800 in which the processor component 850, in executing the control routine 840, collects the playing piece data 837 and transmits it to the collection device 100 either through longer range communications with the AP devices 200 or through shorter range communications with the player devices 400. As recognizable to those skilled in the art, the control routines 140, 440 and 840, including the components of which each is composed, are selected to be operative on whatever type of processor or processors that are selected to implement applicable ones of the processor components 150, 450 or 850.

In various embodiments, each of the control routines 140, 440 and 840 may include one or more of an operating system, device drivers and/or application-level routines (e.g., so-called "software suites" provided on disc media, "applets" obtained from a remote server, etc.). Where an operating system is included, the operating system may be any of a variety of available operating systems appropriate for whatever corresponding ones of the processor components 150, 450 or 850. Where one or more device drivers are included, those device drivers may provide support for any of a variety of other components, whether hardware or software components, of corresponding ones of the computing devices 100, 400 or 800.

The control routines 440 or 840 may include a communications component 449 or 849, respectively, executable by whatever corresponding ones of the processor components 450 or 850 to operate corresponding ones of the interfaces 490 or 890 to transmit and receive signals via one or more of the networks 299 and 699 as has been described. Among those signals may be signals conveying the AP data 132, the pairing data 136, the player data 435 and/or the playing piece data 837 among one or more of the computing devices 100, 200, 400 or 800. As will be recognized by those skilled in the art, each of these communications components is selected to be operable with whatever type of interface technology is selected to implement corresponding ones of the interfaces 490 or 890.

More specifically, the communications components 449 and/or 849 may cooperate with collection device 100 and/or the AP device(s) 200 via the longer range wireless network 299 to perform pairing. Again, in such pairing, the AP device(s) 200 may be caused to recognize the player devices 400 and the playing piece device 800 as participants on the longer range wireless network 299, and the player device(s) 400 and the playing piece device 800 may be caused to recognize the AP device(s) 200 as participants on the longer range wireless network 299. Security credentials may also be exchanged to enable the use of encryption. Further, during such pairing, the communications components 449 and/or 849 may receive at least a portion of the pairing data 136 from the collection device 100 via the longer range wireless network 299 and the AP device(s) 200. The communications component 449 and/or 849 may then use the pairing data 136 to perform pairing directly therebetween via the shorter range wireless network 699. Again, in such pairing, the player device(s) 400 may be caused to recognize the playing piece device 800 as a participant on the shorter range wireless network 699, and the playing piece device 800 may be caused to recognize the player device(s) 400 as participants on the shorter range wireless network 699. Again, security credentials may also be exchanged to enable the use of encryption.

The control routines 440 or 840 may include an interaction detection component 447 or 847, respectively, executable by whatever corresponding ones of the processor components 450 or 850 to operate corresponding ones of the interaction sensors 415 or 815 to detect indications of interaction between the body or bodies 500 of player(s) on which at least one player device 400 is carried and the playing piece 700 into which the playing piece device 800 may be incorporated. Again, the interaction sensors 415 and 815 may each be based on any of a variety of technologies to detect such interaction, including directly or indirectly as has been discussed. As such interactions are detected by the interaction sensor 415, the interaction detection component 447 may store indications of various aspects of such interactions (e.g., type of interaction, speed, direction, force applied, accelerations caused, etc.) as part of the player data 435. Correspondingly, as such interactions are detected by the interaction sensor 815, the interaction detection component 847 may store indications of various aspects of such interactions (e.g., type of interaction, speed, direction, force applied, accelerations caused, etc.)

as part of the playing piece data 837.

As depicted, the communications component 849 may incorporate a power control component 841 executable by the processor component 850 to determine whether to use a lesser amount of electric power from the power source 801 to operate the interface 890 to engage in shorter range communications via the shorter range wireless network 699 or to use a greater amount of electric power to operate the interface 890 to engage in longer range communications via the longer range wireless network 299. Use of the lesser amount of electric power to engage in such shorter range communications may be selected by the power control component 841 in response to an indication from the interaction detection component 847 of the interaction sensor 815 detecting contact with the playing piece 700 and/or movement imparted to the playing piece 700 that may be deemed consistent with interaction with the playing piece 700 by one or more players' bodies 500. Thus, where there are indications of such interaction, the shorter range wireless network 699 may be employed to transmit the playing piece device data 837 to one or more player devices 400 to relay onward to the collection device 100. However, use of the greater amount of electric power to engage in such longer range communications may be selected by the power control component 841 in response to an indication from the interaction detection component 847 of the interaction sensor 815 detecting movement imparted to the playing piece 700 that may be deemed consistent with the playing piece 700 being thrown, kicked or otherwise caused to move a relatively lengthy distance by one or more players. As has been discussed, it may be deemed unlikely that any players' bodies 500 are in close proximity to the playing piece 700 as it undergoes such a lengthy and uninterrupted movement. Thus, where there are indications of such interaction, the longer range wireless network 299 may be employed to transmit the playing piece device data 837 to one or more AP devices 200 to provide the playing piece data 837 more directly to the collection device 100.

The control routine 440 may include a proximity detection component 448 executable by the processor component 450 to operate the proximity sensors 410 to detect the playing piece 700 coming into relatively close proximity of the body 500 that carries a player device 400. Again, the proximity sensor 410 may be based on any of a variety of technologies to detect proximity to the playing piece 700 as has been discussed. As instances of the playing piece 700 being detected as being within a relatively short proximity are detected by the proximity sensor 410, the proximity detection component 448 may store indications of various aspects of such instances (e.g., when, for how long, etc.) as part of the player data 435.

As depicted, the communications component 449 may incorporate a power control component 441 executable by the processor component 450 to determine whether to use electric power from the power source 401 to operate the interface 490 to engage in shorter range communications via the shorter range wireless network 699 and/or to engage in longer range communications via the longer range wireless network 299. Whether to use electric power to engage in either or both of shorter range or longer range communications may be determined by the power control component 441 in response to an indication from the proximity detection component 448 of the proximity sensor 410 detecting that a player's body 500 which carries a player device 400 is within relatively close proximity to the playing piece 700. Thus, where there are indications of such close proximity, the shorter range wireless network 699 may be employed to receive portions of the playing piece data 837 from the playing piece 700 and/or the longer range wireless network 299 may be employed to transmit portions of the player data 435 and/or relay the received portions of the playing piece device data 837 to one or more of the AP devices 200 to convey the player data 435 and/or the playing piece data 837 to the collection device 100. However, where there is no such indication of relatively close proximity, then the use of electric power to engage in at least longer range communications via the longer range wireless network 299 may be restricted by the power control component 441.

However, in alternate embodiments, whether to use electric power to engage in either or both of shorter range or longer range communications may be determined by the power control component 441 in response to both an indication from the proximity detection component 448 of the proximity sensor 410 detecting that the body 500 of a player on which a player device 400 is carried is within relatively close proximity to the playing piece 700, and in response to an indication from the interaction detection component 447 that interactions between the player's body 500 and the playing piece 700 have been detected by the interaction sensor 415. Thus, where there are indications of both such close proximity and such interaction, the shorter range wireless network 699 may be employed to receive portions of the playing piece data 837 from the playing piece 700 and/or the longer range wireless network 299 may be employed to transmit portions of the player data 435 and/or relay the received portions of the playing piece device data 837 to one or more AP devices 200. However, where either of such an indication of relatively close proximity or such an indication of interaction is lacking, then the use of electric power to engage in at least longer range communications via the longer range wireless network 299 may be restricted by the power control component 441.

To enable detection of proximity of the playing piece 700 to a player's body 500, the playing piece device 800 may include a proximity signal emitter 870 to emit a signal selected to enable detection by the proximity sensor 410 of one or more of the player devices 400. As has been discussed, the proximity signal emitter 870 may be made up of one or more magnets incorporated into the playing piece 700 to emit a magnetic field for detection in embodiments in which the proximity sensor 410 is sensitive to such a magnetic field. In such embodiments, no electric energy is required from the power source 401 to effect such emissions.

However, in embodiments in which emission of a signal by the proximity signal emitter 870 does require electric power from the power source 801, the control routine 840 may include an emission control component 844 executable by the processor component 850 to control the use of electric power by the proximity signal emitter 870. In some embodiments, the emission control component 844 may control the proximity signal emitter 870 to use such electric power or to restrict it from using such electric power in response to an indication from the communications component 849 of whether or not electric power is being used to engage in longer range communications as a result of a determination that it is unlikely that the playing piece 700 is currently in close proximity to any players' bodies 500. Thus, it may be deemed desirable to cease to use electric power to operate the proximity signal emitter unless there is an indication that such movement of the playing piece 700 over a lengthy distance has ceased such that there might again be the body or bodies 500 of one or more players in relatively close proximity.

The control routine 440 may include a location detection component 446 executable by the processor component 450 to operate the communications component 490 at times when electric power is used to engage in longer range communications to use signals from multiple AP devices 200 to at least distinguish the current location within the playing area 600 from other locations. However, as also discussed, the AP data 132 may be received from the collection device 100, and the location detection component 446 may use indications of relative strengths of signals from different AP devices 200 and/or relatively locations of the AP devices 200 to analyze the relative strengths of signals received from the multiple AP devices 200 to determine the current location within the playing are 600. As locations of the player device 400 are determined, the location detection component 446 may store indications of those locations on a recurring basis (e.g., at a regular interval) as part of the player data 435. Alternatively or additionally, as locations of the player device 400 are determined and during times when the player device 400 is in communications with the playing piece device 700 via the shorter range wireless network 699, indications of the current location as determined by the location detection device 446 may be transmitted to the playing piece device 800.

The control routine 840 may include a location correlation component 846 executable by the processor component 850 to correlate locations within the playing area 600 to the quality of longer range communications available at those locations. The location correlation component 846 may receive indications of the current quality of longer range communications on a recurring basis from the communications component 849. The location component 846 may also cooperate with the communications component 849 to determine the relative strengths of signals received from multiple ones of the AP devices 200 at the current location. The correlation component 846 may then store indications of correlations between different locations and the quality of longer range communications possible at those locations within the correlation data 836. In some embodiments, the location component 846 may make no effort to correlate a location within the playing area 600 to the relative strengths of signals received from different ones of the AP devices 200. Thus, the detected differing relative strengths of received signals may be employed to distinguish between locations within the playing area 600 without attempting to determine where those locations actually are within the playing area 600. In other embodiments, the correlation component 846 may employ indications of relative strengths with which each AP device 200 transmits signals and/or indications of relative positions of the AP devices 200 found within the AP data 132 to determine where those locations are within the playing area 600. Thus, the differing levels of quality of longer range communications observed at different locations may be correlated to indications of actual locations within the playing area 600 within the correlation data 836.

Alternatively or additionally, the location correlation component 846 may rely on one or more player devices 400 to provide indications of the current location and/or indications of the level of quality of longer range communications possible at those locations via the shorter range wireless network 699 at times when the playing piece device 800 is engaged in shorter range communications with player devices 400. As has been discussed, the indications of the current location received from the player devices 400 may be made up of indications of relative strengths of signals received from the AP devices 200 or may be made up of an indication of a location within the playing area 600 derived by one or more of the player devices 400 from an analysis of the relative strengths of those received signals using the AP data 132.

Figure 7:
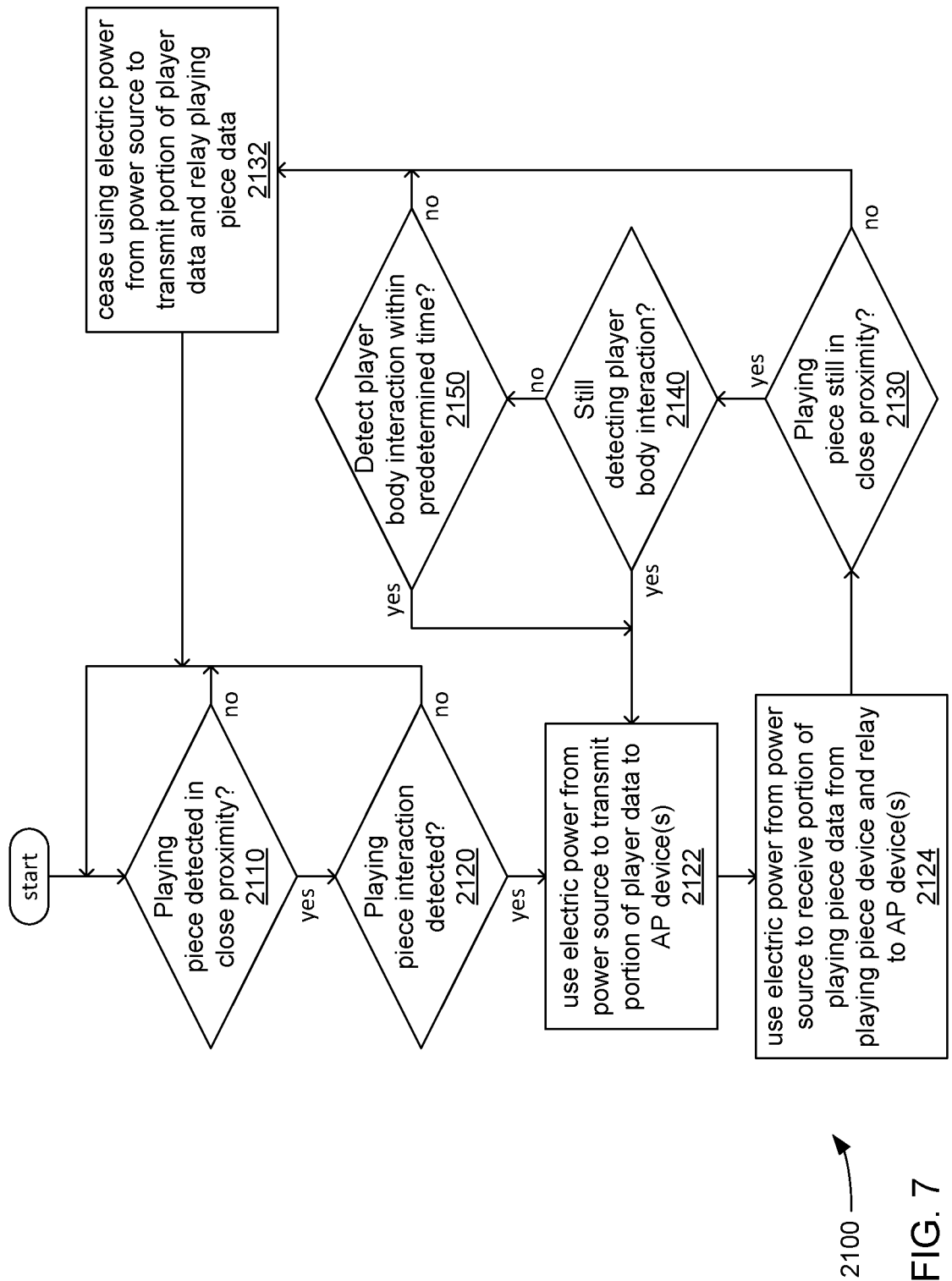
FIGS. 7, 8, 9 and 10 each illustrate a logic flow according to an embodiment.

FIG. 7 illustrates an embodiment of a logic flow 2100. The logic flow 2100 may be representative of some or all of the operations executed by one or more embodiments described herein. More specifically, the logic flow 2100 may illustrate operations performed by at least the processor component 450 in executing at least the control routine 440, and/or performed by other component(s) of at least one of the player devices 400.

At 2110, a processor component of a player device carried on a portion of the body of a player (e.g., the processor component 450 of one of the player devices 400 carried on a portion of the body 500 of a player) operates a proximity detector thereof to determine whether a playing piece is detected in close proximity to the player (e.g., the playing piece 700). As previously discussed, the proximity sensor may be made up of multiple sensing components and/or may be based on any of a variety of technologies to detect when the playing piece is in relatively close proximity. As has also been discussed, the term "relatively close proximity" may be taken as indicating that the playing piece is close enough to the player for the player to reach to it and touch it with a hand and/or with a foot. If the playing piece is not in relatively close proximity to the player at 2110, then the processor component returns to operating the proximity detector to again check for the playing piece coming into relatively close proximity to the player.

However, if the playing piece is in relatively close proximity at 2110, then the processor component operates an interaction detector of the player device to determine whether there is interaction between the player and the playing piece at 2120. As previously discussed, the interaction sensor may be made up of multiple sensing components and/or may be based on any of a variety of technologies to detect when there is interaction between the player and the playing piece. If there is no such interaction at 2120, then the processor component returns to operating the proximity detector to again check for the playing piece coming into relatively close proximity to the player.

However, if there is such interaction at 2120, then the processor component uses electric power from a power source of the player device to operate an interface of the player device that may be accompanied by an antenna to transmit a portion of player data to at least one AP device at 2122. As previously discussed, the at least one AP device is operated by the collection device to receive portions of the player data and of playing piece data. Further, the collection device, the at least one AP device, the player device, the playing piece and/or a playing piece device incorporated into the playing piece may belong to a game play monitoring system (e.g., the collection device 100, one or more of the AP devices 200, one or more of the player devices 400, the playing piece 700 and the playing piece device 800 incorporated into the playing piece 700 may all belong to the game play monitoring system 1000).

At 2124, the processor component may also use electric power from the power source to operate the interface to receive a portion of the playing piece data from the playing piece device incorporated into the playing piece, and to then operate the interface to relay that portion to the at least one AP device. As previously discussed, the interface may incorporate more than one transceiver, one of which may be selected and/or configured for longer range communications (e.g., with the one or more AP devices at some distance away across a playing area) and another of which may be selected and/or configured for shorter range communications (e.g., with the playing piece device in relatively close proximity).

At 2130, the processor component may again operate the proximity detector to determine whether the playing piece is still in relatively close proximity to the player. If not, then the processor component may cease use of electric power (e.g., disable provision of electric power) from the power source to operate the interface to transmit a portion of the player data and/or to relay portions of the playing piece data to the one or more AP devices at 2132, before returning to awaiting an indication of the playing piece coming back into relatively close proximity to the player at 2110.

However, if the playing piece is still in relatively close proximity to the player at 2130, then the processor component may again operate the interaction detector to determine if there is still ongoing interaction between the player and the playing piece. If so, then the processor component may continue to enable use of electric power to operate the interface to transmit another portion of the player data to the at least one AP device at 2122, and to both receive and relay portions of the playing piece data from the playing piece device at 2124.

However, if there is no such ongoing player interaction at 2140, then the processor component may again operate the interaction detector to monitor for a return of such player interaction during a predetermined period of time at 2150. If no such player interaction occurs within the predetermined period of time at 2150, then the processor component may discontinue use of electric power as earlier described at 2132. However, if such player interaction does occur within the predetermined period of time at 2150, then the processor component may return to using electric power as earlier described at 2122 and 2124. As has been discussed, the while the playing piece may remain within a relatively close proximity to a player on an uninterrupted basis, a player's interaction with the playing piece may be made up of multiple instances of interaction separated by a various amounts of time. The predetermined period of time may be selected to allow for up to a selected maximum amount of time to pass between instances of interaction without triggering a cessation of the use of electric power in transmitting at least portions of player data via longer range communications.

Figure 8:
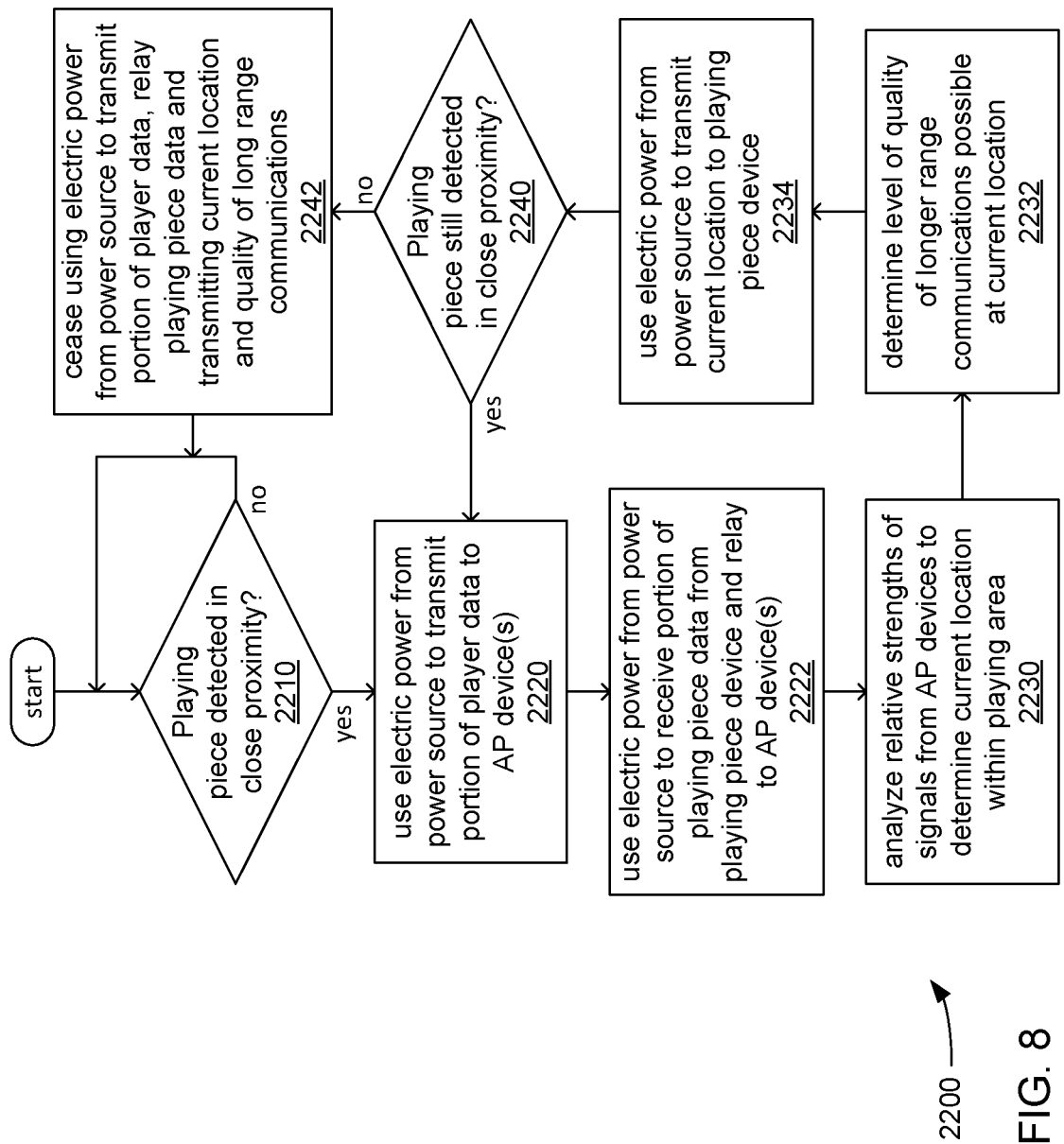

FIG. 8 illustrates an embodiment of a logic flow 2200. The logic flow 2200 may be representative of some or all of the operations executed by one or more embodiments described herein. More specifically, the logic flow 2200 may illustrate operations performed by at least the processor component 450 in executing at least the control routine 440, and/or performed by other component(s) of at least one of the player devices 400.

At 2210, a processor component of a player device carried on a portion of the body of a player (e.g., the processor component 450 of one of the player devices 400 carried on a portion of the body 500 by a player) operates a proximity detector thereof to determine whether a playing piece is detected in close proximity to the player (e.g., the playing piece 700). Again, the term "relatively close proximity" may be taken as indicating that the playing piece is close enough to the player for the player to reach to it and touch it with a hand and/or with a foot. If the playing piece is not in relatively close proximity to the player at 2210, then the processor component returns to operating the proximity detector to again check for the playing piece coming into relatively close proximity to the player.

However, if the playing piece is in relatively close proximity at 2210, then the processor component uses electric power from a power source of the player device to operate an interface of the player device that may be accompanied by an antenna to transmit a portion of player data to at least one AP device at 2220 to be ultimately received by a collection device. As previously discussed, the at least one AP device is operated by the collection device to receive portions of the player data and of playing piece data.

At 2222, the processor component may also use electric power from the power source to operate the interface to receive a portion of playing piece data from the playing piece device incorporated into the playing piece, and to then operate the interface to relay that portion to the at least one AP device. Again, the interface may incorporate more than one transceiver, one of which may be selected and/or configured for longer range communications (e.g., with the one or more AP devices at some distance away across a playing area) and another of which may be selected and/or configured for shorter range communications (e.g., with the playing piece device in relatively close proximity).

At 2230, the processor component may further operate the interface to analyze the relative strengths of the signals received from multiple ones of the AP devices to determine the current location of the player device within the playing area. As previously discussed, the player device may receive AP data conveying indications of relative strengths of signals transmitted by the AP devices and/or of relative locations of the AP devices, and may employ those indications in analyzing the relative signal strengths of signals received from the AP devices. The AP devices may so provide the AP data under the control of the collection device, which may store the AP data and/or be manually operated to generate the AP data. At 2232, the processor component may additionally determine a level of quality of longer range communications that are possible at the current location. At 2234, the processor component may further use electric power from the power source to operate the interface to transmit indications of the current location and the level of quality of longer range communications available at the current location to the playing piece device.

At 2240, the processor component may again operate the proximity detector to determine whether the playing piece is still in relatively close proximity to the player. If not, then the processor component may cease use of electric power (e.g., disable provision of electric power) from the power source to operate the interface to transmit a portion of the player data and relay portions of the playing piece data to the one or more AP devices, and/or to transmit a current location and level of quality of longer range communications at the current location to the playing piece device at 2242, before returning to awaiting an indication of the playing piece coming back into relatively close proximity to the player at 2210. However, if the playing piece is still in relatively close proximity to the player at 2240, then the processor component may continue to enable use of electric power to operate the interface to transmit another portion of the player data and relay portions of the playing piece data to the at least one AP device at 2220, and/or to transmit the current location and the level of quality of longer range communications at the current location to the playing piece device at 2222.

Figure 9:
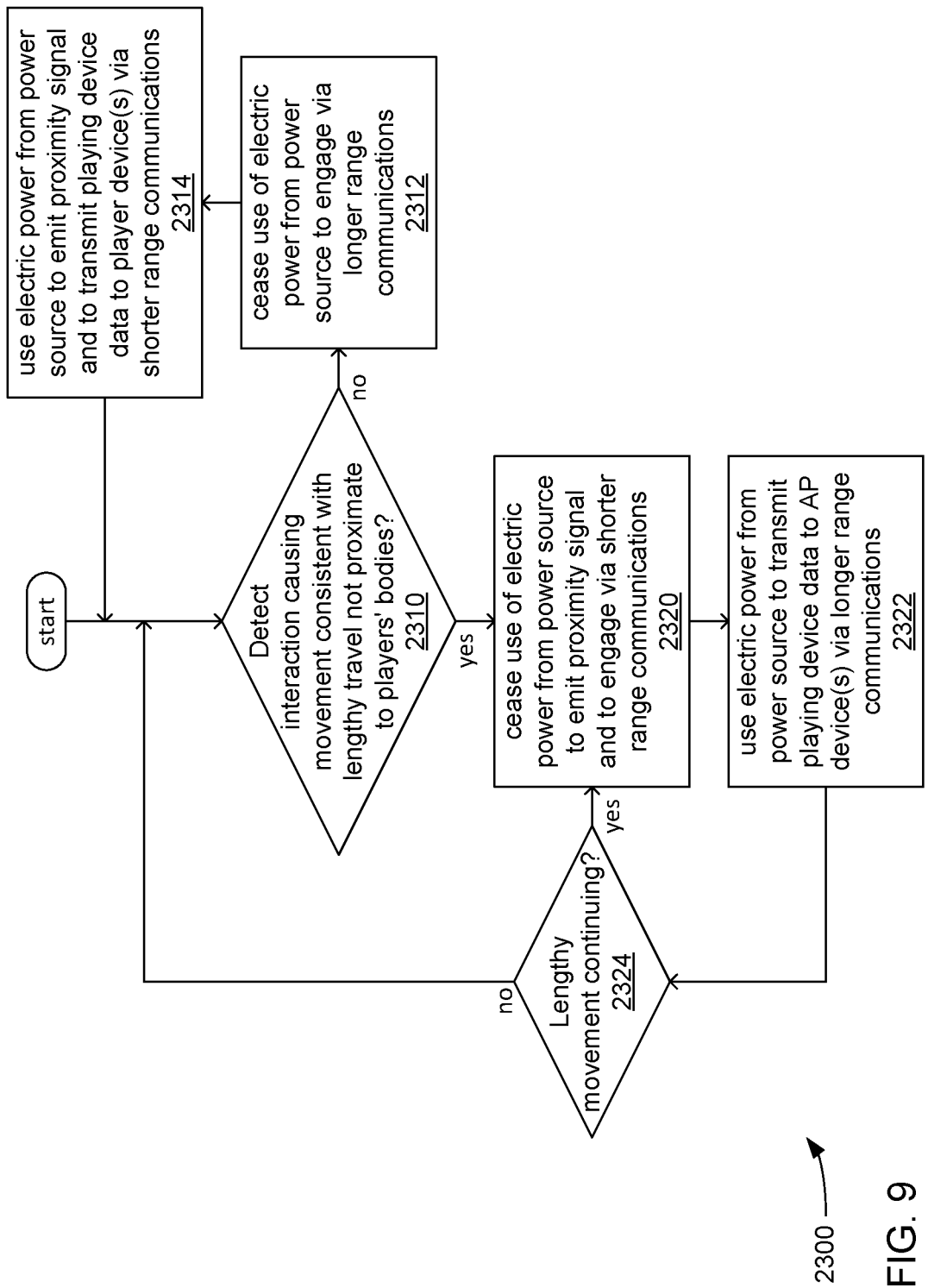

FIG. 9 illustrates an embodiment of a logic flow 2300. The logic flow 2300 may be representative of some or all of the operations executed by one or more embodiments described herein. More specifically, the logic flow 2300 may illustrate operations performed by at least the processor component 850 in executing at least the control routine 840, and/or performed by other component(s) of the playing piece device 800.

At 2310, a processor component of a playing piece device incorporated into a playing piece (e.g., the processor component 850 of the playing piece device 800 incorporated into the playing piece 700) operates an interaction detector thereof to determine whether there is interaction between a player and the playing piece that is consistent with an interaction that imparts enough force to impart a lengthy travel movement to the playing piece. More precisely, if an interaction imparts an amount of force exceeding a threshold of force to put the playing piece in motion for at least an amount of time exceeding a threshold of time such that a lengthy distance is traveled before another interaction is detected that changes the movement, then the determination may be made at 2310 that a lengthy movement has been detected that has taken the playing piece away from being in relatively close proximity to any player. As previously discussed, the interaction sensor may be made up of multiple sensing components and/or may be based on any of a variety of technologies to detect when there is interaction between the player and the playing piece.

If the processor component determines at 2310 that such a lengthy movement has not been caused, then the processor component may disable any use currently underway of electric power from a power source of the playing piece device to engage in longer range communications at 2312. The processor component may then use electric power from that power source at 2314 to operate a proximity signal emitter to emit a signal that may be detectable by a proximity detector of a player device carried on a portion of the body of a player. As previously discussed, the proximity signal that is emitted may be any of a variety of types of signal, including and not limited to a radio frequency signal, an acoustic signal or a magnetic signal (e.g., a magnetic field). The processor component may also operate, at 2314, an interface of the playing piece device that may be accompanied by an antenna to transmit a portion of playing piece data via shorter range communications to at least one player device carried on a portion of the body of a player, before returning to operating the interaction detector to detect an interaction at 2310.

However, if the processor component determines at 2310 that such a lengthy movement has been caused, then the processor component may disable any use currently underway of electric power from a power source of the playing piece device to emit a proxy signal or to engage in shorter range communications at 2320. The processor component may then use electric power from that power source at 2322 to operate the interface to transmit a portion of the playing piece data via longer range communications to at least one AP device to be ultimately received by a collection device. As previously discussed, the at least one AP device is operated by the collection device to receive portions of the playing piece data and of player data. Further, the collection device, the at least one AP device, the playing piece, the playing piece device incorporated into the playing piece and/or at least one player device may belong to a game play monitoring system (e.g., the collection device 100, one or more of the AP devices 200, one or more of the player devices 400, the playing piece 700 and the playing piece device 800 incorporated into the playing piece 700 may all belong to the game play monitoring system 1000).

At 2324, the processor component may again operate the interaction detector (which as has been discussed may include one or more motion sensing components) to determine if the lengthy movement of the playing piece is still ongoing, or if the playing piece has been interacted with in a manner that changed the movement. If the lengthy movement continues at 2324, then the processor component may continue to disable use of electric power as earlier described at 2320 and may continue to use electric power as earlier described at 2322. However, if the lengthy movement is not continuing at 2324, then the processor component may return to operating the interaction detector to detect an interaction at 2310

Figure 10:
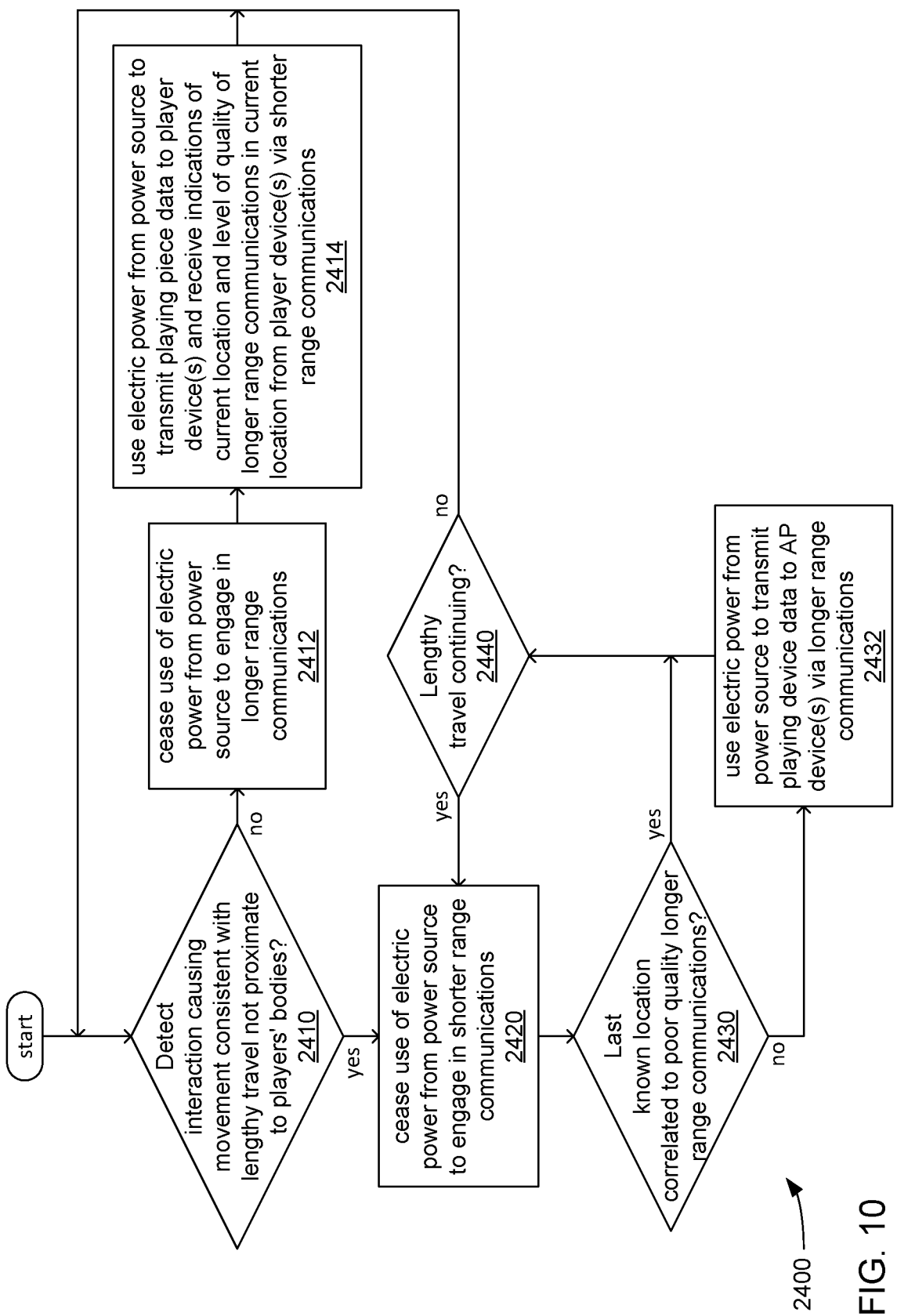

FIG. 10 illustrates an embodiment of a logic flow 2400. The logic flow 2400 may be representative of some or all of the operations executed by one or more embodiments described herein. More specifically, the logic flow 2400 may illustrate operations performed by at least the processor component 850 in executing at least the control routine 840, and/or performed by other component(s) of the playing piece device 800.

At 2410, a processor component of a playing piece device incorporated into a playing piece (e.g., the processor component 850 of the playing piece device 800 incorporated into the playing piece 700) operates an interaction detector thereof to determine whether there is interaction between a player and the playing piece that is consistent with an interaction that imparts enough force to impart a lengthy travel movement to the playing piece. More precisely, if an interaction imparts an amount of force exceeding a threshold of force to put the playing piece in motion for at least an amount of time exceeding a threshold of time such that a lengthy distance is traveled before another interaction is detected that changes the movement, then the determination may be made at 2410 that a lengthy movement has been detected that has taken the playing piece away from being in relatively close proximity to any player.

If the processor component determines at 2410 that such a lengthy movement has not been caused, then the processor component may disable any use currently underway of electric power from a power source of the playing piece device to engage in longer range communications at 2412. The processor component may then use electric power from that power source at 2414 to operate an interface of the playing piece device that may be accompanied by an antenna to transmit a portion of playing piece data via shorter range communications to at least one player device carried on a portion of the body of a player. The processor component may also operate the interface to receive indications of the current location of the player currently interacting with the playing piece and of the level of quality of longer range communications available at the current location, and the processor component may store indications of correlations between locations and the level of quality of longer range communications at those locations before returning to operating the interaction detector to detect an interaction at 2410.

However, if the processor component determines at 2410 that such a lengthy movement has been caused, then the processor component may disable any use currently underway of electric power from a power source of the playing piece device to engage in shorter range communications at 2420. The processor component may then check at 2430 whether the last known current location provided to the playing piece device by a player device via shorter range communications was a location that correlates to a poor level of quality of longer range communications at 2430.

If that last known current location does not correlate to a poor level of quality of longer range communications at 2430, then the processor component may use electric power from that power source at 2322 to operate the interface to transmit a portion of the playing piece data via longer range communications to at least one AP device to be ultimately received by a collection device. Again, the at least one AP device is operated by the collection device to receive portions of the playing piece data and of player data. Further, the collection device, the at least one AP device, the playing piece, the playing piece device incorporated into the playing piece and/or at least one player device may belong to a game play monitoring system (e.g., the collection device 100, one or more of the AP devices 200, one or more of the player devices 400, the playing piece 700 and the playing piece device 800 incorporated into the playing piece 700 may all belong to the game play monitoring system 1000).

At 2440, the processor component may then operate the interaction detector again to determine if the lengthy movement of the playing piece is still ongoing, or if the playing piece has been interacted with in a manner that changed the movement. If the lengthy movement continues at 2440, then the processor component may continue to disable use of electric power as earlier described at 2420. However, if the lengthy movement is not continuing at 2440, then the processor component may return to operating the interaction detector to detect an interaction at 2410.

However, if the last known current location received from a player device does correlate to a poor level of quality of longer range communications at 2430, then the processor component may perform the check of whether the lengthy movement is continuing at 2440 without using electric power as described at 2432.

Figure 11:
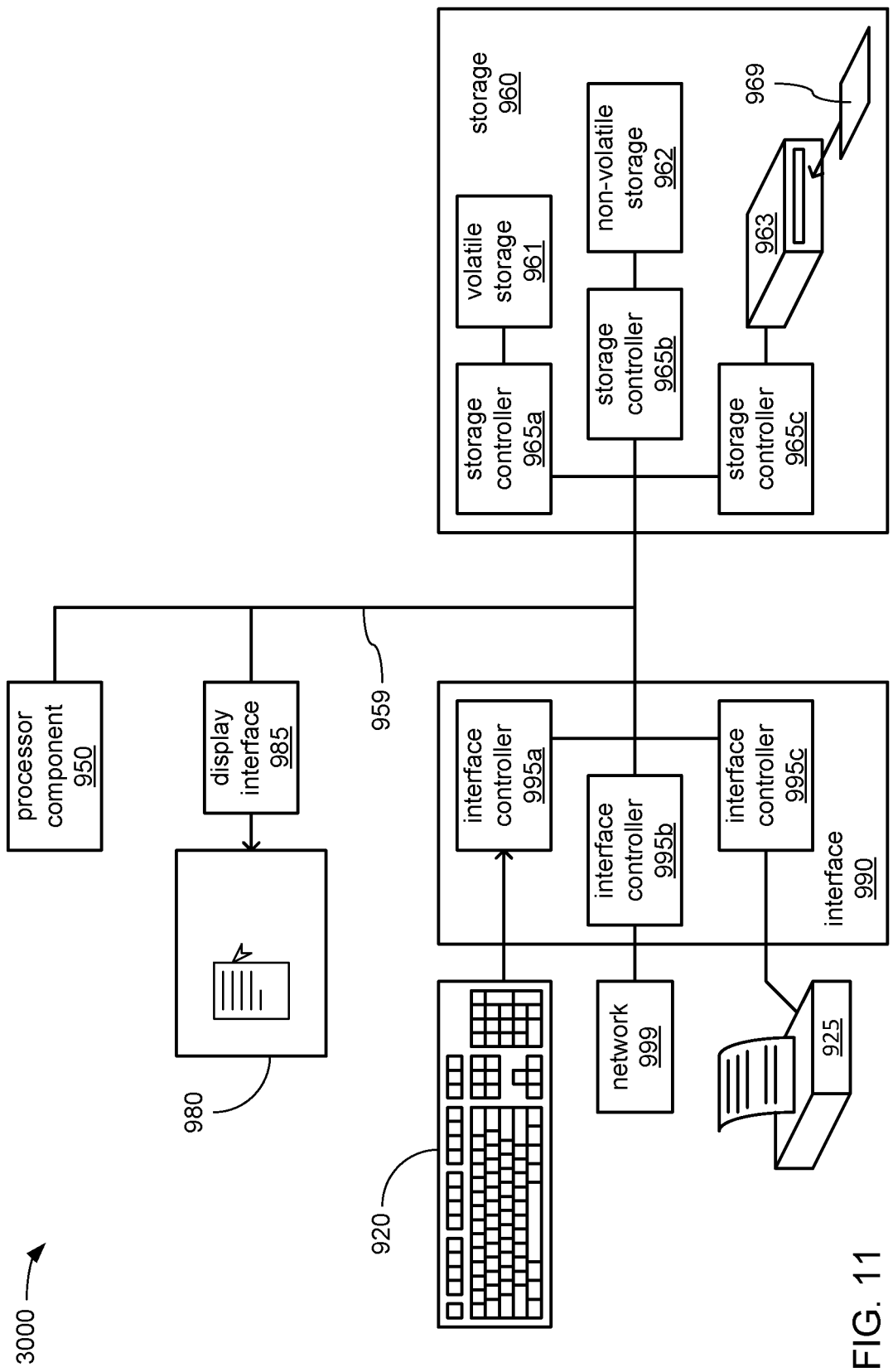
FIG. 11 illustrates a processing architecture according to an embodiment.

FIG. 11 illustrates an embodiment of an exemplary processing architecture 3000 suitable for implementing various embodiments as previously described. More specifically, the processing architecture 3000 (or variants thereof) may be implemented as part of one or more of the computing devices 100, 200, 400 or 800. It should be noted that components of the processing architecture 3000 are given reference numbers in which the last two digits correspond to the last two digits of reference numbers of at least some of the components earlier depicted and described as part of the computing devices 100, 200, 400 and 800. This is done as an aid to correlating components of each.

The processing architecture 3000 includes various elements commonly employed in digital processing, including without limitation, one or more processors, multi-core processors, co-processors, memory units, chipsets, controllers, peripherals, interfaces, oscillators, timing devices, video cards, audio cards, multimedia input/output (I/O) components, power supplies, etc. As used in this application, the terms "system" and "component" are intended to refer to an entity of a computing device in which digital processing is carried out, that entity being hardware, a combination of hardware and software, software, or software in execution, examples of which are provided by this depicted exemplary processing architecture. For example, a component can be, but is not limited to being, a process running on a processor component, the processor component itself, a storage device (e.g., a hard disk drive, multiple storage drives in an array, etc.) that may employ an optical and/or magnetic storage medium, a software object, an executable sequence of instructions, a thread of execution, a program, and/or an entire computing device (e.g., an entire computer). By way of illustration, both an application running on a server and the server can be a component. One or more components can reside within a process and/or thread of execution, and a component can be localized on one computing device and/or distributed between two or more computing devices. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to one or more signal lines. A message (including a command, status, address or data message) may be one of such signals or may be a plurality of such signals, and may be transmitted either serially or substantially in parallel through any of a variety of connections and/or interfaces.

As depicted, in implementing the processing architecture 3000, a computing device includes at least a processor component 950, a storage 960, an interface 990 to other devices, and a coupling 959. As will be explained, depending on various aspects of a computing device implementing the processing architecture 3000, including its intended use and/or conditions of use, such a computing device may further include additional components, such as without limitation, a display interface 985.

The coupling 959 includes one or more buses, point-to-point interconnects, transceivers, buffers, crosspoint switches, and/or other conductors and/or logic that communicatively couples at least the processor component 950 to the storage 960. Coupling 959 may further couple the processor component 950 to one or more of the interface 990, the audio subsystem 970 and the display interface 985 (depending on which of these and/or other components are also present). With the processor component 950 being so coupled by couplings 959, the processor component 950 is able to perform the various ones of the tasks described at length, above, for whichever one(s) of the aforedescribed computing devices implement the processing architecture 3000. Coupling 959 may be implemented with any of a variety of technologies or combinations of technologies by which signals are optically and/or electrically conveyed. Further, at least portions of couplings 959 may employ timings and/or protocols conforming to any of a wide variety of industry standards, including without limitation, Accelerated Graphics Port (AGP), CardBus, Extended Industry Standard Architecture (E-ISA), Micro Channel Architecture (MCA), NuBus, Peripheral Component Interconnect (Extended) (PCI-X), PCI Express (PCI-E), Personal Computer Memory Card International Association (PCMCIA) bus, HyperTransport™, QuickPath, and the like.

As previously discussed, the processor component 950 (corresponding to the processor components 150, 450 and 850) may include any of a wide variety of commercially available processors, employing any of a wide variety of technologies and implemented with one or more cores physically combined in any of a number of ways.

As previously discussed, the storage 960 (corresponding to the storages 160, 460 and 860) may be made up of one or more distinct storage devices based on any of a wide variety of technologies or combinations of technologies. More specifically, as depicted, the storage 960 may include one or more of a volatile storage 961 (e.g., solid state storage based on one or more forms of RAM technology), a non-volatile storage 962 (e.g., solid state, ferromagnetic or other storage not requiring a constant provision of electric power to preserve their contents), and a removable media storage 963 (e.g., removable disc or solid state memory card storage by which information may be conveyed between computing devices). This depiction of the storage 960 as possibly including multiple distinct types of storage is in recognition of the commonplace use of more than one type of storage device in computing devices in which one type provides relatively rapid reading and writing capabilities enabling more rapid manipulation of data by the processor component 950 (but possibly using a "volatile" technology constantly requiring electric power) while another type provides relatively high density of non-volatile storage (but likely provides relatively slow reading and writing capabilities).

Given the often different characteristics of different storage devices employing different technologies, it is also commonplace for such different storage devices to be coupled to other portions of a computing device through different storage controllers coupled to their differing storage devices through different interfaces. By way of example, where the volatile storage 961 is present and is based on RAM technology, the volatile storage 961 may be communicatively coupled to coupling 959 through a storage controller 965a providing an appropriate interface to the volatile storage 961 that perhaps employs row and column addressing, and where the storage controller 965a may perform row refreshing and/or other maintenance tasks to aid in preserving information stored within the volatile storage 961. By way of another example, where the non-volatile storage 962 is present and includes one or more ferromagnetic and/or solid-state disk drives, the non-volatile storage 962 may be communicatively coupled to coupling 959 through a storage controller 965b providing an appropriate interface to the non-volatile storage 962 that perhaps employs addressing of blocks of information and/or of cylinders and sectors. By way of still another example, where the removable media storage 963 is present and includes one or more optical and/or solid-state disk drives employing one or more pieces of machine-readable storage medium 969, the removable media storage 963 may be communicatively coupled to coupling 959 through a storage controller 965c providing an appropriate interface to the removable media storage 963 that perhaps employs addressing of blocks of information, and where the storage controller 965c may coordinate read, erase and write operations in a manner specific to extending the lifespan of the machine-readable storage medium 969.

One or the other of the volatile storage 961 or the non-volatile storage 962 may include an article of manufacture in the form of a machine-readable storage media on which a routine including a sequence of instructions executable by the processor component 950 may be stored, depending on the technologies on which each is based. By way of example, where the non-volatile storage 962 includes ferromagnetic-based disk drives (e.g., so-called "hard drives"), each such disk drive typically employs one or more rotating platters on which a coating of magnetically responsive particles is deposited and magnetically oriented in various patterns to store information, such as a sequence of instructions, in a manner akin to storage medium such as a floppy diskette. By way of another example, the non-volatile storage 962 may be made up of banks of solid-state storage devices to store information, such as sequences of instructions, in a manner akin to a compact flash card. Again, it is commonplace to employ differing types of storage devices in a computing device at different times to store executable routines and/or data. Thus, a routine including a sequence of instructions to be executed by the processor component 950 may initially be stored on the machine-readable storage medium 969, and the removable media storage 963 may be subsequently employed in copying that routine to the non-volatile storage 962 for longer term storage not requiring the continuing presence of the machine-readable storage medium 969 and/or the volatile storage 961 to enable more rapid access by the processor component 950 as that routine is executed.

As previously discussed, the interface 990 (possibly corresponding to the interfaces 190, 290, 490 or 590) may employ any of a variety of signaling technologies corresponding to any of a variety of communications technologies that may be employed to communicatively couple a computing device to one or more other devices. Again, one or both of various forms of wired or wireless signaling may be employed to enable the processor component 950 to interact with input/output devices (e.g., the depicted example keyboard 920 or printer 925) and/or other computing devices, possibly through a network (e.g., the network 999) or an interconnected set of networks. In recognition of the often greatly different character of multiple types of signaling and/or protocols that must often be supported by any one computing device, the interface 990 is depicted as including multiple different interface controllers 995a, 995b and 995c. The interface controller 995a may employ any of a variety of types of wired digital serial interface or radio frequency wireless interface to receive serially transmitted messages from user input devices, such as the depicted keyboard 920. The interface controller 995b may employ any of a variety of cabling-based or wireless signaling, timings and/or protocols to access other computing devices through the depicted network 999 (perhaps a network made up of one or more links, smaller networks, or perhaps the Internet). More specifically, the interface controller 995b may incorporate one or more radio frequency (RF) transceivers and/or may be coupled to one or more antennae 991 (which may be incorporated into a portion of the interface 990) to exchange RF wireless signals with antenna(e) of one or more other devices as part of wireless communications on the depicted network 999. The interface 995c may employ any of a variety of electrically conductive cabling enabling the use of either serial or parallel signal transmission to convey data to the depicted printer 925. Other examples of devices that may be communicatively coupled through one or more interface controllers of the interface 990 include, without limitation, a microphone to monitor sounds of persons to accept commands and/or data signaled by those persons via voice or other sounds they may make, remote controls, stylus pens, card readers, finger print readers, virtual reality interaction gloves, graphical input tablets, joysticks, other keyboards, retina scanners, the touch input component of touch screens, trackballs, various sensors, a camera or camera array to monitor movement of persons to accept commands and/or data signaled by those persons via gestures and/or facial expressions, laser printers, inkjet printers, mechanical robots, milling machines, etc.

Where a computing device is communicatively coupled to (or perhaps, actually incorporates) a display (e.g., the depicted example display 980), such a computing device implementing the processing architecture 3000 may also include the display interface 985. Although more generalized types of interface may be employed in communicatively coupling to a display, the somewhat specialized additional processing often required in visually displaying various forms of content on a display, as well as the somewhat specialized nature of the cabling-based interfaces used, often makes the provision of a distinct display interface desirable. Wired and/or wireless signaling technologies that may be employed by the display interface 985 in a communicative coupling of the display 980 may make use of signaling and/or protocols that conform to any of a variety of industry standards, including without limitation, any of a variety of analog video interfaces, Digital Video Interface (DVI), DisplayPort, etc.

More generally, the various elements of the computing devices described and depicted herein may include various hardware elements, software elements, or a combination of both. Examples of hardware elements may include devices, logic devices, components, processors, microprocessors, circuits, processor components, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. However, determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other. Furthermore, aspects or elements from different embodiments may be combined.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

Although the description and example embodiments presented herein focus largely on the monitoring of interactions between a playing piece and the bodies of one or more players of a game, it should again be noted that what is described and claimed herein may be applied to other contexts. Stated differently, what is described and claimed herein may be applicable to the monitoring of interactions of a wider variety between an interaction object with participants in such interactions. By way of example, what is described herein may be applicable to an interaction object that interacts with portions of bodies of persons who engage in interactions with the interaction object in a context entirely unrelated to game play.

Alternatively or additionally, the playing piece may more broadly be any of a variety of types of interaction object that is interacted with by participants in interaction that may be machines or persons that engage in interactions with the interaction object in a context unrelated to sports. In one such example, the playing piece may be an instrument package to be ejected into a weather system from a vehicle. The vehicle may carry players who are personnel engaged in studying a weather system. While on board such a vehicle, the instrument package may detect interactions with machinery and/or the personnel within the vehicle providing that may be deemed likely to maintain the interaction object in relatively close proximity thereto. As a result, the instrument package may employ electric power from its own power source to engage in shorter range wireless communications while on board. During such communications, various pieces of data may be transmitted to the instrument package, including an indication of the current location of the vehicle, as well as settings and/or indications of portions of the weather system in which longer range wireless communications may be more difficult may be transmitted to the interaction object. However, upon being placed into a launch tube and/or otherwise interacted with in preparation for being ejected into the weather system, and then upon being ejected into the weather system, the instrument package may detect such interaction as being consistent with causing lengthy travel away from a relatively close proximity to any participant. As a result, the instrument package may cease to employ electric power to engage in the shorter range wireless communications and may switch to employing its electric power to engage in longer range wireless communications back to the vehicle, where the longer range wireless communications may consume electric power at a greater rate. Further, upon reaching a location within the weather system in which longer range communications may be more difficult such that the level of quality of longer range communications may be reduced, the instrument package may temporarily refrain from using electric power to engage in longer range communications until entering into another location within the weather system that is not correlated to such a reduced level of quality of longer range communications.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims. The detailed disclosure now turns to providing examples that pertain to further embodiments. The examples provided below are not intended to be limiting.

In Example 1, an apparatus to monitor interactions includes an interaction detection component to monitor an interaction sensor incorporated into a playing piece to detect an interaction of the playing piece with a portion of a body, to generate playing piece data recording an aspect of the interaction and to determine whether the interaction maintains the playing piece within a close proximity to the body; and a communications component to use electric power from a power source to wirelessly transmit the playing piece data to a player device carried on the body via shorter range wireless communications or to wirelessly transmit the playing piece data to an access point (AP) device via longer range wireless communications based on the determination, the shorter range wireless communications to consume electric power of the power source at a lesser rate than the longer range wireless communications.

In Example 2, which includes the subject matter of Example 1, the interaction detection component may determine whether the interaction maintains the playing piece within the close proximity based on at least one of an amount of force applied to the playing piece or an amount of time the playing piece remains in an uninterrupted motion following an application of force to the playing piece.

In Example 3, which includes the subject matter of any of Examples 1-2, the interaction detection component may compare the amount of force applied to a threshold of force applied and to compare the amount of time to a threshold of time to determine whether the interaction maintains the playing piece within the close proximity.

In Example 4, which includes the subject matter of any of Examples 1-3, the apparatus may include a proximity signal emitter to emit a signal to enable the player device to detect the proximity of the playing piece to the body, and an emission control component to selectively provide electric power from the power source to the proximity signal emitter based on the determination.

In Example 5, which includes the subject matter of any of Examples 1-4, the proximity signal emitter may include an acoustic driver to emit a sound with an amplitude selected to be detectable by the player device while the playing piece is within the close proximity to the body.

In Example 6, which includes the subject matter of any of Examples 1-5, the apparatus may include at least one magnet carried by an external surface portion of the playing piece to emit a magnetic field detectable by the player device while the playing piece is within the close proximity to the body.

In Example 7, which includes the subject matter of any of Examples 1-6, the apparatus may include a location correlation component to condition transmission of the playing piece data via the longer range wireless communications on whether a last known location of the playing piece within a playing area is correlated to a poor level of quality of the longer range wireless communications.

In Example 8, which includes the subject matter of any of Examples 1-7, the last known location may include a location of the player device within the playing area at a time when the playing piece is within the close proximity to the body, the communications component to wirelessly receive an indication from the player device of the last known location and of a level of quality of longer range wireless communications correlated to the last known location via the shorter range wireless communications.

In Example 9, which includes the subject matter of any of Examples 1-8, the body may include a body of a player of a game, and the close proximity to the body consisting of one of a distance of up to one meter from the body, a distance from the body of up to a limit of reach by a hand of the body, and a distance from the body of up to a limit of reach by a foot of the body In Example 10, which includes the subject matter of any of Examples 1-9, the apparatus may include an antenna and an interface coupled to the antenna to transmit the playing piece data via the shorter range wireless communications and via the longer range wireless communications.

In Example 11, an apparatus to monitor interactions includes an proximity detection component to monitor a proximity sensor incorporated into a player device to detect a proximity of a playing piece to a body that carries the player device and to determine whether the playing piece is within a close proximity to the body; an interaction detection component to monitor an interaction sensor incorporated into the player device to detect an interaction of a portion of the body with the playing piece and to generate at least a portion of a player data recording an aspect of the interaction; and a communications component to use electric power from a power source of the player device to wirelessly transmit the player data and playing piece data to an access point (AP) device via longer range wireless communications based on the determination and based on detection of the interaction, the playing piece data received from the playing piece via shorter range wireless communications, the shorter range wireless communications to consume electric power of the power source at a lesser rate than the longer range wireless communications.

In Example 12, which includes the subject matter of Example 11, the interaction detection component may generate another portion of the player data recording an indication of when the playing piece is in close proximity to the body.

In Example 13, which includes the subject matter of any of Examples 11-12, the apparatus may include the proximity sensor, and the proximity sensor may include at least one of a microphone to detect a sound emitted by the playing piece, a reed switch to detect a magnetic field emitted by the playing piece, or an interface coupled to an antenna to detect a radio frequency emitted by the playing piece to engage in the shorter range wireless communications with the player device.

In Example 14, which includes the subject matter of any of Examples 11-13, the apparatus may include an antenna; an interface coupled to the antenna to receive radio frequency signals emitted by at least the AP device to engage in the longer range wireless communications; and a location detection component to analyze the radio frequency signals received by the interface from multiple AP devices to determine a current location of the player device within a playing area, the multiple AP devices may include the AP device, and the communications component to transmit an indication of the current location to the playing piece via the shorter range wireless communications.

In Example 15, which includes the subject matter of any of Examples 11-14, the location component may analyze relative strengths of the radio frequency signals received from the multiple AP devices to determine the current location using at least one of an indication of relative positions of the multiple AP devices received from the AP device via the longer range wireless communications or an indication of relative strengths of transmission of signals of the multiple AP devices received from the AP device via the longer range wireless communications.

In Example 16, which includes the subject matter of any of Examples 11-15, the communications component may analyze a level of quality of the longer range wireless communications at the current location and to transmit an indication of the level of quality at the current location to the playing piece via the shorter range wireless communications.

In Example 17, which includes the subject matter of any of Examples 11-16, the communications component may use electric power from the power source to wirelessly receive the playing piece data from the playing device via the shorter range wireless communications based on the determination and based on detection of the interaction.

In Example 18, which includes the subject matter of any of Examples 11-17, the apparatus may include the power source, and the power source may include a battery.

In Example 19, which includes the subject matter of any of Examples 11-18, the body may include a body of a player of a game, and the close proximity to the body consisting of one of a distance of up to one meter from the body, a distance from the body of up to a limit of reach by a hand of the body, and a distance from the body of up to a limit of reach by a foot of the body.

In Example 20, which includes the subject matter of any of Examples 11-19, the apparatus may include an antenna and an interface coupled to the antenna to transmit the playing piece data via the shorter range wireless communications and via the longer range wireless communications.

In Example 21, a computing-implemented method for monitoring interactions includes monitoring an interaction sensor incorporated into a playing piece to detect an interaction of the playing piece with a portion of a body; generating playing piece data recording an aspect of the interaction; determining whether the interaction maintains the playing piece within a close proximity to the body; and using electric power from the power source to wirelessly transmit the playing piece data to a player device carried on the body via shorter range wireless communications or to wirelessly transmit the playing piece data to an access point (AP) device via longer range wireless communications based on the determination, the shorter range wireless communications to consume electric power of the power source at a lesser rate than the longer range wireless communications.

In Example 22, which includes the subject matter of Example 21, the method may include determining whether the interaction maintains the playing piece within the close proximity based on at least one of an amount of force applied to the playing piece or an amount of time the playing piece remains in an uninterrupted motion following an application of force to the playing piece.

In Example 23, which includes the subject matter of any of Examples 21-22, the method may include comparing the amount of force applied to a threshold of force applied; and comparing the amount of time to a threshold of time to determine whether the interaction maintains the playing piece within the close proximity In Example 24, which includes the subject matter of any of Examples 21-23, the method may include using electric power from the power source to emit a signal to enable the player device to detect the proximity of the playing piece to the body based on the determination.

In Example 25, which includes the subject matter of any of Examples 21-24, the method may include emitting a sound with an amplitude selected to be detectable by the player device while the playing piece is within the close proximity to the body.

In Example 26, which includes the subject matter of any of Examples 21-25, the method may include emitting a magnetic field detectable by the player device while the playing piece is within the close proximity to the body.

In Example 27, which includes the subject matter of any of Examples 21-26, the method may include conditioning transmission of the playing piece data via the longer range wireless communications on whether a last known location of the playing piece within a playing area is correlated to a poor level of quality of the longer range wireless communications.

In Example 28, which includes the subject matter of any of Examples 21-27, the last known location may include a location of the player device within the playing area at a time when the playing piece is within the close proximity to the body, and the method may include wirelessly receiving an indication from the player device of the last known location and of a level of quality of longer range wireless communications correlated to the last known location via the shorter range wireless communications.

In Example 29, which includes the subject matter of any of Examples 21-28, the body may include a body of a player of a game, and the close proximity to the body consisting of one of a distance of up to one meter from the body, a distance from the body of up to a limit of reach by a hand of the body, and a distance from the body of up to a limit of reach by a foot of the body.

In Example 30, which includes the subject matter of any of Examples 21-29, the playing piece may include an antenna to transmit the playing piece data via the shorter range wireless communications and via the longer range wireless communications.

In Example 31, a computing-implemented method for monitoring interactions includes monitoring a proximity sensor incorporated into a player device to detect a proximity of a playing piece to a portion of a body that carries the player device; determining whether the playing piece is within a close proximity to the body; monitoring an interaction sensor incorporated into the player device to detect an interaction of the body with the playing piece; generating at least a portion of a player data recording an aspect of the interaction; and using electric power from a power source of the player device to wirelessly transmit the player data and playing piece data to an access point (AP) device via longer range wireless communications based on the determination and based on detection of the interaction, the playing piece data received from the playing piece via shorter range wireless communications, the shorter range wireless communications to consume electric power of the power source at a lesser rate than the longer range wireless communications.

In Example 32, which includes the subject matter of Example 31, the method may include generating another portion of the player data recording an indication of when the playing piece is in close proximity to the body.

In Example 33, which includes the subject matter of any of Examples 31-32, detecting proximity of the playing piece to the body may include at least one of detecting a sound emitted by the playing piece, detecting a magnetic field emitted by the playing piece, or detecting a radio frequency emitted by the playing piece to engage in the shorter range wireless communications with the player device.

In Example 34, which includes the subject matter of any of Examples 31-33, the method may include receiving radio frequency signals emitted by at least the AP device to engage in the longer range wireless communications; analyzing the radio frequency signals received by the interface from multiple AP devices to determine a current location of the player device within a playing area, the multiple AP devices may include the AP device; and transmitting an indication of the current location to the playing piece via the shorter range wireless communications.

In Example 35, which includes the subject matter of any of Examples 31-34, the method may include analyzing relative strengths of the radio frequency signals received from the multiple AP devices to determine the current location using at least one of an indication of relative positions of the multiple AP devices received from the AP device via the longer range wireless communications or an indication of relative strengths of transmission of signals of the multiple AP devices received from the AP device via the longer range wireless communications.

In Example 36, which includes the subject matter of any of Examples 31-35, the method may include analyzing a level of quality of the longer range wireless communications at the current location; and transmitting an indication of the level of quality at the current location to the playing piece via the shorter range wireless communications.

In Example 37, which includes the subject matter of any of Examples 31-36, the method may include using electric power from the power source to wirelessly receive the playing piece data from the playing device via the shorter range wireless communications based on the determination and based on detection of the interaction.

In Example 38, which includes the subject matter of any of Examples 31-37, the power source may include a battery.

In Example 39, which includes the subject matter of any of Examples 31-38, the body may include a body of a player of a game, and the close proximity to the body consisting of one of a distance of up to one meter from the body, a distance from the body of up to a limit of reach by a hand of the body, and a distance from the body of up to a limit of reach by a foot of the body.

In Example 40, which includes the subject matter of any of Examples 31-39, the player device may include an antenna to transmit the playing piece data via the shorter range wireless communications and via the longer range wireless communications.

In Example 41, at least one machine-readable storage medium includes instructions that when executed by a computing device, cause the computing device to monitor an interaction sensor incorporated into a playing piece to detect an interaction of the playing piece with a portion of a body; generate playing piece data recording an aspect of the interaction; determine whether the interaction maintains the playing piece within a close proximity to the body; and use electric power from the power source to wirelessly transmit the playing piece data to a player device carried by the body via shorter range wireless communications or to wirelessly transmit the playing piece data to an access point (AP) device via longer range wireless communications based on the determination, the shorter range wireless communications to consume electric power of the power source at a lesser rate than the longer range wireless communications.

In Example 42, which includes the subject matter of Example 41, the computing device may be caused to determine whether the interaction maintains the playing piece within the close proximity based on at least one of an amount of force applied to the playing piece or an amount of time the playing piece remains in an uninterrupted motion following an application of force to the playing piece.

In Example 43, which includes the subject matter of any of Examples 41-42, the computing device may be caused to compare the amount of force applied to a threshold of force applied, and compare the amount of time to a threshold of time to determine whether the interaction maintains the playing piece within the close proximity.

In Example 44, which includes the subject matter of any of Examples 41-43, the computing device may be caused to use electric power from the power source to emit a signal to enable the player device to detect the proximity of the playing piece to the body based on the determination.

In Example 45, which includes the subject matter of any of Examples 41-44, the computing device may be caused to emit a sound with an amplitude selected to be detectable by the player device while the playing piece is within the close proximity to the body.

In Example 46, which includes the subject matter of any of Examples 41-45, the computing device may be caused to emit a magnetic field detectable by the player device while the playing piece is within the close proximity to the body.

In Example 47, which includes the subject matter of any of Examples 41-46, the computing device may be caused to condition transmission of the playing piece data via the longer range wireless communications on whether a last known location of the playing piece within a playing area is correlated to a poor level of quality of the longer range wireless communications.

In Example 48, which includes the subject matter of any of Examples 41-47, the last known location may include a location of the player device within the playing area at a time when the playing piece is within the close proximity to the body, and the processor component caused to wirelessly receive an indication from the player device of the last known location and of a level of quality of longer range wireless communications correlated to the last known location via the shorter range wireless communications.

In Example 49, which includes the subject matter of any of Examples 41-48, the body may include a body of a player of a game, and the close proximity to the body consisting of one of a distance of up to one meter from the body, a distance from the body of up to a limit of reach by a hand of the body, and a distance from the body of up to a limit of reach by a foot of the body.

In Example 50, which includes the subject matter of any of Examples 41-49, the playing piece may include an antenna to transmit the playing piece data via the shorter range wireless communications and via the longer range wireless communications.

In Example 51, at least one machine-readable storage medium includes instructions that when executed by a computing device, cause the computing device to monitor a proximity sensor incorporated into a player device to detect a proximity of a playing piece to a portion of a body that carries the player device; determine whether the playing piece is within a close proximity to the body; monitor an interaction sensor incorporated into the player device to detect an interaction of the body with the playing piece; generate at least a portion of a player data recording an aspect of the interaction; and use electric power from a power source of the player device to wirelessly transmit the player data and playing piece data to an access point (AP) device via longer range wireless communications based on the determination and based on detection of the interaction, the playing piece data received from the playing piece via shorter range wireless communications, the shorter range wireless communications to consume electric power of the power source at a lesser rate than the longer range wireless communications.

In Example 52, which includes the subject matter of Example 51, the computing device may be caused to generate another portion of the player data recording an indication of when the playing piece is in close proximity to the body.

In Example 53, which includes the subject matter of any of Examples 51-52, detecting proximity of the playing piece to the body may include at least one of detecting a sound emitted by the playing piece, detecting a magnetic field emitted by the playing piece, or detecting a radio frequency emitted by the playing piece to engage in the shorter range wireless communications with the player device.

In Example 54, which includes the subject matter of any of Examples 51-53, the computing device may be caused to receive radio frequency signals emitted by at least the AP device to engage in the longer range wireless communications; analyze the radio frequency signals received by the interface from multiple AP devices to determine a current location of the player device within a playing area, the multiple AP devices including the AP device; and transmit an indication of the current location to the playing piece via the shorter range wireless communications.

In Example 55, which includes the subject matter of any of Examples 51-54, the computing device may be caused to analyze relative strengths of the radio frequency signals received from the multiple AP devices to determine the current location using at least one of an indication of relative positions of the multiple AP devices received from the AP device via the longer range wireless communications or an indication of relative strengths of transmission of signals of the multiple AP devices received from the AP device via the longer range wireless communications.

In Example 56, which includes the subject matter of any of Examples 51-55, the computing device may be caused to analyze a level of quality of the longer range wireless communications at the current location, and transmit an indication of the level of quality at the current location to the playing piece via the shorter range wireless communications.

In Example 57, which includes the subject matter of any of Examples 51-56, the computing device may be caused to use electric power from the power source to wirelessly receive the playing piece data from the playing device via the shorter range wireless communications based on the determination and based on detection of the interaction.

In Example 58, which includes the subject matter of any of Examples 51-57, the power source may include a battery.

In Example 59, which includes the subject matter of any of Examples 51-58, the body may include a body of a player of a game, and the close proximity to the body consisting of one of a distance of up to one meter from the body, a distance from the body of up to a limit of reach by a hand of the body, and a distance from the body of up to a limit of reach by a foot of the body.

In Example 60, which includes the subject matter of any of Examples 51-59, the player device may include an antenna to transmit the playing piece data via the shorter range wireless communications and via the longer range wireless communications.

In Example 61, at least one machine-readable storage medium may include instructions that when executed by a computing device, cause the computing device to perform any of the above.

In Example 62, an apparatus to monitor interactions may include means for performing any of the above.

In Example 63, a system to monitor interactions includes a power source; an interaction detection component to monitor an interaction sensor incorporated into a playing piece to detect an interaction of the playing piece with a portion of a body, to generate playing piece data recording an aspect of the interaction and to determine whether the interaction maintains the playing piece within a close proximity to the body; a communications component to use electric power from the power source to wirelessly transmit the playing piece data to a player device carried on the body via shorter range wireless communications or to wirelessly transmit the playing piece data to an access point (AP) device via longer range wireless communications based on the determination, the shorter range wireless communications to consume electric power of the power source at a lesser rate than the longer range wireless communications; and an antenna and an interface coupled to the antenna to transmit the playing piece data via the shorter range wireless communications and via the longer range wireless communications.

In Example 64, which includes the subject matter of Example 63, the system may include a proximity signal emitter to emit a signal to enable the player device to detect the proximity of the playing piece to the body, and an emission control component to selectively provide electric power from the power source to the proximity signal emitter based on the determination.

In Example 65, which includes the subject matter of any of Examples 63-64, the proximity signal emitter may include an acoustic driver to emit a sound with an amplitude selected to be detectable by the player device while the playing piece is within the close proximity to the body.

In Example 66, which includes the subject matter of any of Examples 63-65, the system may include at least one magnet carried by an external surface portion of the playing piece to emit a magnetic field detectable by the player device while the playing piece is within the close proximity to the body.

In Example 67, which includes the subject matter of any of Examples 63-66, the system may include a location correlation component to condition transmission of the playing piece data via the longer range wireless communications on whether a last known location of the playing piece within a playing area is correlated to a poor level of quality of the longer range wireless communications.

The invention claimed is:

1. An apparatus, comprising:
    a sensor;
    a first transmitter;
    a processor coupled to the sensor and the transmitter; and
    memory coupled to the processor, the memory comprising instructions, which when executed by the processor, cause the processor to:
        receive at least one indication from the sensor;
        generate game playing piece data based on the at least one indication;
        determine, based on the at least one indication, whether the apparatus is predicted to move an amount greater than a threshold value; and
        transmit, via the first transmitter, at least a portion of the game playing piece data to an access point (AP) based on a determination that the apparatus is predicted to move an amount greater than the threshold value.

2. The apparatus of claim 1, comprising a proximity signal emitter coupled to the processor, the memory comprising instructions that when executed by the processor, cause the processor to send a control signal to the proximity signal emitter to cause the proximity signal emitter to power down based on a determination that the apparatus is to move greater than the threshold value.

3. The apparatus of claim 1, the memory comprising instructions that when executed by the processor, cause the processor to send a control signal to the first transmitter to cause the first transmitter to power down based on a determination that the apparatus is not to move greater than the threshold value.

4. The apparatus of claim 1, comprising a proximity signal emitter coupled to the processor and comprising a second transmitter coupled to the processor, the second transmitter arranged to wirelessly transmit signals over a shorter range than the first transmitter, the memory comprising instructions that when executed by the processor, cause the processor to:
    transmit, via the proximity signal emitter, a proximity signal;
    detect a proximity to a player device based on the proximity signal emitted by the proximity signal emitter; and
    transmit, via the second transmitter instead of the first transmitter, the at least the portion of the playing piece data to the player device based on the detected proximity to the player device.

5. The apparatus of claim 4, the memory comprising instructions that when executed by the processor, cause the processor to:
    receive, from the player device, an indication of a signal quality associated with the first transmitter;
    delay transmitting, via the first transmitter, the at least the portion of the playing piece data to the AP based on a determination that the apparatus is to move greater than the threshold value and a determination that the signal quality associated with the first transmitter is less than a specified quality level.

6. The apparatus of claim 5, the memory comprising instructions that when executed by the processor, cause the processor to send a control signal to the second transmitter to cause the second transmitter to power down based on the detected proximity to the player device.

7. The apparatus of claim 1, comprising a power source selectively coupled to the first transmitter.

8. The apparatus of claim 1, the sensor comprising at least one of a shock detector, a contact detector, a gyroscope, or an accelerometer.

9. At least one non-transitory computer-readable medium, comprising instructions that when executed by a processor, cause the processor to:
    receive at least one indication from a sensor coupled to the processor;
    generate game playing piece data based on the at least one indication;
    determine, based on the at least one indication, whether the indication corresponds to an amount of movement predicted to be greater than a threshold value; and
    transmit, via a first transmitter, at least a portion of the game playing piece data to an access point (AP) based on a determination that the predicted movement amount is greater than the threshold value.

10. The at least one non-transitory computer-readable medium of claim 9, comprising instructions that when executed by the processor, cause the processor to send a control signal to a proximity signal emitter to cause the proximity signal emitter to power down based on a determination that the movement is greater than the threshold value.

11. The at least one non-transitory computer-readable medium of claim 9, comprising instructions that when executed by the processor, cause the processor to send a control signal to the first transmitter to cause the first transmitter to power down based on a determination that the movement is greater than the threshold value.

12. The at least one non-transitory computer-readable medium of claim 9, comprising instructions that when executed by the processor, cause the processor to:
    transmit, via a proximity signal emitter, a proximity signal;
    detect a proximity to a player device based on the proximity signal emitted by the proximity signal emitter; and
    transmit, via a second transmitter instead of the first transmitter, the at least the portion of the game playing piece data to the player device based on the detected proximity to the player device.

13. The at least one non-transitory computer-readable medium of claim 12, comprising instructions that when executed by the processor, cause the processor to:
    receive, from the player device, an indication of a signal quality associated with the first transmitter;
    delay transmitting, via the first transmitter, the at least the portion of the playing piece data to the AP based on a determination that the movement is greater than the threshold value and a determination that the signal quality associated with the first transmitter is less than a specified quality level.

14. The at least one non-transitory computer-readable medium of claim 13, comprising instructions that when executed by the processor, cause the processor to send a control signal to the second transmitter to cause the second transmitter to power down based on the detected proximity to the player device.

15. A game playing piece, comprising:
a sensor;
a first transmitter;
processing logic coupled to the sensor and the transmitter; and
memory coupled to the processing logic, the memory comprising instructions, which when executed by the processing logic, cause the processing logic to:
receive signals from the sensor, the signals indicating an interaction with the game playing piece;
determine, based on the received signals, whether the game playing piece is predicted to move an amount greater than a threshold value; and
transmit, via the first transmitter, an information element including an indication of the interaction to an access point (AP) based on a determination that the game playing piece is predicted to move an amount greater than the threshold value.

16. The playing piece of claim 15, wherein the interaction with the game playing piece is contact between the playing piece and a player.

17. The game playing piece of claim 15, comprising a proximity signal emitter coupled to the processing logic, the memory comprising instructions that when executed by the processing logic, cause the processing logic to send a control signal to the proximity signal emitter to cause the proximity signal emitter to power down based on a determination that the game playing piece is to move greater than the threshold value.

18. The game playing piece of claim 15, the memory comprising instructions that when executed by the processing logic, cause the processing logic to send a control signal to the first transmitter to cause the first transmitter to power down based on a determination that the game playing piece is not to move greater than the threshold value.

19. The game playing piece of claim 15, comprising a proximity signal emitter coupled to the processing logic and comprising a second transmitter coupled to the processing logic, the second transmitter arranged to wirelessly transmit signals over a shorter range than the first transmitter, the memory comprising instructions that when executed by the processing logic, cause the processing logic to:
transmit, via the proximity signal emitter, a proximity signal;
detect a proximity to a player device based on the proximity signal emitted by the proximity signal emitter; and
transmit, via the second transmitter instead of the first transmitter, the information element to the player device based on the detected proximity to the player device.

20. The game playing piece of claim 19, the memory comprising instructions that when executed by the processing logic, cause the processing logic to:
receive, from the player device, an indication of a signal quality associated with the first transmitter;
delay transmitting, via the first transmitter, the information element to the AP based on a determination that the game playing piece is to move greater than the threshold value and a determination that the signal quality associated with the first transmitter is less than a specified quality level.

21. The game playing piece of claim 20, the memory comprising instructions that when executed by the processing logic, cause the processing logic to send a control signal to the second transmitter to cause the second transmitter to power down based on the detected proximity to the player device.

22. The game playing piece of claim 15, comprising a power source selectively coupled to the first transmitter.

23. The game playing piece of claim 15, the sensor comprising at least one of a shock detector, a contact detector, a gyroscope, or an accelerometer.

* * * * *